(12) United States Patent
Alferness

(10) Patent No.: US 8,021,385 B2
(45) Date of Patent: Sep. 20, 2011

(54) REMOVABLE ANCHORED LUNG VOLUME REDUCTION DEVICES AND METHODS

(75) Inventor: Clifton A. Alferness, Redmond, WA (US)

(73) Assignee: Spiration, Inc., Redmond, WA (US)

( * ) Notice: Subject to any disclaimer, the term of this patent is extended or adjusted under 35 U.S.C. 154(b) by 937 days.

(21) Appl. No.: 11/880,090

(22) Filed: Jul. 19, 2007

(65) Prior Publication Data

US 2008/0119866 A1    May 22, 2008

Related U.S. Application Data

(63) Continuation of application No. 10/103,487, filed on Mar. 20, 2002, now abandoned.

(51) Int. Cl.
*A61M 29/00* (2006.01)
(52) U.S. Cl. .............. 606/191; 623/23.64; 128/205.19
(58) Field of Classification Search ............... 606/108, 606/190–192; 604/167.01, 167.04, 174, 604/500, 506; 128/207.14, 207.15, 205.19; 623/23.64, 23.65, 9, 23.68
See application file for complete search history.

(56) References Cited

U.S. PATENT DOCUMENTS

| | | | |
|---|---|---|---|
| 2,479,805 A | 8/1949 | Batchell |
| 2,832,078 A | 4/1958 | Williams |
| 2,981,254 A | 4/1961 | Vanderbilt |
| 3,320,972 A | 5/1967 | High et al. |
| 3,370,305 A | 2/1968 | Goott et al. |
| 3,445,916 A | 5/1969 | Schulte |
| 3,472,230 A | 10/1969 | Forgarty |
| 3,540,431 A | 11/1970 | Modin-Uddin |
| 3,617,060 A | 11/1971 | Iezzi |
| 3,657,744 A | 4/1972 | Ersek |
| 3,671,979 A | 6/1972 | Moulopoulos |
| 3,683,913 A | 8/1972 | Kurtz et al. |
| 3,757,783 A | 9/1973 | Alley |
| 3,760,808 A | 9/1973 | Bleuer |
| 3,788,327 A | 1/1974 | Donowitz et al. |
| 3,874,388 A | 4/1975 | King et al. |
| 4,014,318 A | 3/1977 | Dockum et al. |

(Continued)

FOREIGN PATENT DOCUMENTS

AU    2002239759    5/2002

(Continued)

OTHER PUBLICATIONS

Japanese Office Action Received in 2003-577779 Dated Feb. 3, 2009.

(Continued)

*Primary Examiner* — Victor Nguyen
(74) *Attorney, Agent, or Firm* — Knobbe, Martens, Olson & Bear, LLP

(57) ABSTRACT

A method for treating a lung using an intra-bronchial device may be placed and anchored in an air passageway of a patient to collapse a lung portion associated with the air passageway. The method includes using an obstructing member that prevents air from being inhaled into the lung portion, and an anchor that anchors the obstruction device within the air passageway. The anchor may piercingly engage the air passageway wall. The anchor may be releasable from the air passageway for removal of the obstructing member. The anchor may be releasable by collapsing a portion of the obstructing member, or by drawing the obstructing member toward the larynx. The obstructing member may be a one-way valve.

8 Claims, 14 Drawing Sheets

U.S. PATENT DOCUMENTS

| | | |
|---|---|---|
| 4,040,428 A | 8/1977 | Clifford |
| 4,056,854 A | 11/1977 | Boretos et al. |
| 4,084,268 A | 4/1978 | Ionescu et al. |
| 4,086,665 A | 5/1978 | Poirier |
| 4,212,463 A | 7/1980 | Repinski et al. |
| 4,218,782 A | 8/1980 | Rygg |
| 4,222,126 A | 9/1980 | Boretos et al. |
| 4,250,873 A | 2/1981 | Bonnet |
| 4,301,810 A | 11/1981 | Belman |
| 4,302,854 A | 12/1981 | Runge |
| 4,339,831 A | 7/1982 | Johnson |
| RE31,040 E | 9/1982 | Possis |
| 4,403,616 A | 9/1983 | King |
| 4,456,016 A | 6/1984 | Nowacki et al. |
| 4,512,338 A | 4/1985 | Balko et al. |
| 4,533,137 A | 8/1985 | Sonne |
| 4,569,674 A | 2/1986 | Phillips et al. |
| 4,582,058 A | 4/1986 | Depel et al. |
| 4,592,741 A | 6/1986 | Vincent |
| 4,601,465 A | 7/1986 | Roy |
| 4,610,256 A | 9/1986 | Wallace |
| 4,619,246 A | 10/1986 | Molgaard-Nielsen et al. |
| 4,654,027 A | 3/1987 | Dragan et al. |
| 4,654,029 A | 3/1987 | D'Antonio |
| 4,681,110 A | 7/1987 | Wiktor |
| 4,684,363 A | 8/1987 | Ari et al. |
| 4,685,908 A | 8/1987 | Kurtz |
| 4,710,192 A | 12/1987 | Liotta et al. |
| 4,727,873 A | 3/1988 | Mobin-Uddin |
| 4,732,152 A | 3/1988 | Wallsten et al. |
| 4,745,925 A | 5/1988 | Dietz |
| 4,759,758 A | 7/1988 | Gabbay |
| 4,795,449 A | 1/1989 | Schneider et al. |
| 4,808,183 A | 2/1989 | Panje |
| 4,819,664 A | 4/1989 | Nazari |
| 4,822,354 A | 4/1989 | Elosegui |
| 4,830,003 A | 5/1989 | Wolff et al. |
| 4,832,680 A | 5/1989 | Haber et al. |
| 4,846,836 A | 7/1989 | Reich |
| 4,850,999 A | 7/1989 | Planck |
| 4,852,568 A | 8/1989 | Kensey |
| 4,877,025 A | 10/1989 | Hanson |
| 4,908,028 A | 3/1990 | Colon et al. |
| 4,934,999 A | 6/1990 | Bader |
| 4,936,823 A * | 6/1990 | Colvin et al. ..................... 600/7 |
| 4,968,294 A | 11/1990 | Salama |
| 4,973,047 A | 11/1990 | Norell |
| 4,979,505 A | 12/1990 | Cox |
| 4,984,581 A | 1/1991 | Stice |
| 5,033,312 A | 7/1991 | Stupecky |
| 5,038,621 A | 8/1991 | Stupecky |
| 5,059,208 A | 10/1991 | Coe et al. |
| 5,061,274 A | 10/1991 | Kensey |
| 5,078,739 A | 1/1992 | Martin |
| 5,092,781 A | 3/1992 | Casciotti et al. |
| 5,116,360 A | 5/1992 | Pinchuk et al. |
| 5,116,564 A | 5/1992 | Jansen et al. |
| 5,123,919 A | 6/1992 | Sauter et al. |
| 5,135,488 A | 8/1992 | Foote et al. |
| 5,151,105 A | 9/1992 | Kwan-Gett |
| 5,158,548 A | 10/1992 | Lau et al. |
| 5,161,524 A | 11/1992 | Evans |
| 5,171,299 A | 12/1992 | Heitzmann et al. |
| 5,197,980 A | 3/1993 | Gorshkov et al. |
| 5,255,687 A | 10/1993 | McKenna |
| 5,275,169 A | 1/1994 | Afromowitz et al. |
| 5,283,063 A | 2/1994 | Freeman |
| 5,300,050 A | 4/1994 | Everett, Jr. et al. |
| 5,304,199 A | 4/1994 | Myers |
| 5,306,234 A | 4/1994 | Johnson |
| 5,314,473 A | 5/1994 | Godin |
| 5,339,805 A | 8/1994 | Parker |
| 5,342,298 A | 8/1994 | Michaels |
| 5,352,240 A | 10/1994 | Ross |
| 5,353,470 A | 10/1994 | Bartlett |
| 5,358,518 A | 10/1994 | Camilli |
| 5,366,478 A | 11/1994 | Brinkerhoff et al. |
| 5,370,657 A | 12/1994 | Irie |
| 5,382,261 A | 1/1995 | Palmaz |
| 5,383,470 A | 1/1995 | Kolby |
| 5,391,205 A | 2/1995 | Knight |
| 5,392,775 A | 2/1995 | Adkins, Jr. et al. |
| 5,398,844 A | 3/1995 | Zaslavsky et al. |
| 5,409,019 A | 4/1995 | Wilk |
| 5,409,444 A | 4/1995 | Kensey et al. |
| 5,411,507 A | 5/1995 | Heckele |
| 5,411,552 A | 5/1995 | Andersen et al. |
| 5,413,599 A | 5/1995 | Imachi et al. |
| 5,415,660 A | 5/1995 | Campbell et al. |
| 5,417,226 A | 5/1995 | Juma |
| 5,421,325 A | 6/1995 | Cinberg et al. |
| 5,445,626 A | 8/1995 | Gigante |
| 5,453,090 A | 9/1995 | Martenez et al. |
| 5,459,544 A | 10/1995 | Emura |
| 5,484,444 A | 1/1996 | Braunschweiler et al. |
| 5,486,154 A | 1/1996 | Kelleher |
| 5,499,995 A | 3/1996 | Teirstein |
| 5,500,014 A | 3/1996 | Quijano et al. |
| RE35,225 E | 4/1996 | Herweck et al. |
| 5,507,754 A | 4/1996 | Green et al. |
| 5,507,797 A | 4/1996 | Suzuki |
| 5,509,900 A | 4/1996 | Kirkman |
| 5,514,153 A * | 5/1996 | Bonutti ..................... 606/190 |
| 5,549,626 A | 8/1996 | Miller et al. |
| 5,549,628 A | 8/1996 | Cooper et al. |
| 5,562,608 A | 10/1996 | Sekins et al. |
| 5,562,641 A | 10/1996 | Flomenblit et al. |
| 5,562,728 A | 10/1996 | Lazarus et al. |
| 5,603,698 A | 2/1997 | Roberts et al. |
| 5,607,469 A | 3/1997 | Frey |
| 5,645,565 A | 7/1997 | Rudd et al. |
| 5,647,857 A | 7/1997 | Andersen et al. |
| 5,660,175 A | 8/1997 | Dayal |
| 5,662,622 A | 9/1997 | Gore et al. |
| 5,662,713 A | 9/1997 | Andersen et al. |
| 5,669,933 A | 9/1997 | Simon et al. |
| 5,676,671 A | 10/1997 | Inoue |
| 5,683,451 A | 11/1997 | Lenker et al. |
| 5,690,644 A | 11/1997 | Yurek et al. |
| 5,693,089 A | 12/1997 | Inoue |
| 5,697,968 A | 12/1997 | Rogers et al. |
| 5,702,343 A | 12/1997 | Alferness |
| 5,702,409 A | 12/1997 | Rayburn et al. |
| 5,725,519 A | 3/1998 | Penner et al. |
| 5,752,522 A | 5/1998 | Murphy |
| 5,752,965 A | 5/1998 | Francis et al. |
| 5,755,770 A | 5/1998 | Ravenscroft |
| 5,763,979 A | 6/1998 | Mukherjee et al. |
| 5,782,896 A | 7/1998 | Chen et al. |
| 5,797,920 A | 8/1998 | Kim |
| 5,797,960 A | 8/1998 | Stevens et al. |
| 5,800,339 A | 9/1998 | Salama |
| 5,803,078 A | 9/1998 | Brauner |
| 5,810,837 A | 9/1998 | Hofmann et al. |
| 5,817,101 A | 10/1998 | Fiedler |
| 5,830,217 A | 11/1998 | Ryan |
| 5,833,694 A | 11/1998 | Poncet |
| 5,840,081 A | 11/1998 | Andersen et al. |
| 5,851,232 A | 12/1998 | Lois |
| 5,855,587 A | 1/1999 | Hyon |
| 5,855,597 A | 1/1999 | Jayaraman |
| 5,855,601 A | 1/1999 | Bessler et al. |
| 5,865,724 A | 2/1999 | Palmer et al. |
| 5,876,434 A | 3/1999 | Flomenblit et al. |
| 5,876,445 A | 3/1999 | Andersen et al. |
| 5,911,756 A | 6/1999 | Debry |
| 5,925,063 A | 7/1999 | Khosravi |
| 5,944,738 A | 8/1999 | Amplatz et al. |
| 5,947,997 A | 9/1999 | Pavcnik et al. |
| 5,954,636 A | 9/1999 | Schwartz et al. |
| 5,954,766 A | 9/1999 | Zadno-Azizi et al. |
| 5,957,949 A | 9/1999 | Leonhardt et al. |
| 5,957,978 A | 9/1999 | Blom |
| 5,972,009 A | 10/1999 | Fortier et al. |
| 5,976,158 A | 11/1999 | Adams et al. |
| 5,976,174 A | 11/1999 | Ruiz |
| 5,984,965 A | 11/1999 | Knapp et al. |

| | | | |
|---|---|---|---|
| 5,989,234 A | 11/1999 | Valerio et al. | |
| 6,003,517 A | 12/1999 | Sheffield et al. | |
| 6,007,575 A | 12/1999 | Samuels | |
| 6,009,614 A | 1/2000 | Morales | |
| 6,010,511 A | 1/2000 | Murphy | |
| 6,010,525 A | 1/2000 | Bonutti et al. | |
| 6,020,380 A | 2/2000 | Killian | |
| 6,027,525 A | 2/2000 | Suh et al. | |
| 6,045,560 A | 4/2000 | McKean et al. | |
| 6,051,022 A | 4/2000 | Cai et al. | |
| 6,062,575 A | 5/2000 | Mickel et al. | |
| 6,068,635 A | 5/2000 | Gianotti | |
| 6,068,638 A | 5/2000 | Makower | |
| 6,077,291 A | 6/2000 | Das | |
| 6,079,413 A | 6/2000 | Baran | |
| 6,083,141 A | 7/2000 | Hougen | |
| 6,083,255 A | 7/2000 | Laufer et al. | |
| 6,096,027 A | 8/2000 | Layne | |
| 6,099,551 A | 8/2000 | Gabbay | |
| 6,123,663 A | 9/2000 | Rebuffat | |
| 6,132,458 A | 10/2000 | Staehle et al. | |
| 6,135,729 A | 10/2000 | Aber | |
| 6,135,991 A | 10/2000 | Muni et al. | |
| 6,141,855 A | 11/2000 | Morales | |
| 6,146,357 A | 11/2000 | Addis | |
| 6,149,664 A | 11/2000 | Kurz | |
| 6,162,245 A | 12/2000 | Jayaraman | |
| 6,165,179 A | 12/2000 | Cathcart et al. | |
| 6,168,614 B1 | 1/2001 | Andersen et al. | |
| 6,168,617 B1 | 1/2001 | Blaeser et al. | |
| 6,174,307 B1 | 1/2001 | Daniel et al. | |
| 6,174,323 B1 | 1/2001 | Biggs | |
| 6,183,520 B1 | 2/2001 | Pintauro et al. | |
| 6,193,748 B1 | 2/2001 | Thompson et al. | |
| 6,200,333 B1 | 3/2001 | Laufer | |
| 6,203,551 B1 | 3/2001 | Wu | |
| 6,206,918 B1 | 3/2001 | Campbell et al. | |
| 6,210,338 B1 | 4/2001 | Afremov et al. | |
| 6,231,587 B1 * | 5/2001 | Makower | 606/198 |
| 6,231,589 B1 | 5/2001 | Wessman et al. | |
| 6,234,996 B1 | 5/2001 | Bagaoisan et al. | |
| 6,238,334 B1 | 5/2001 | Easterbrook, III et al. | |
| 6,240,615 B1 | 6/2001 | Kimes et al. | |
| 6,241,654 B1 | 6/2001 | Alferness | |
| 6,241,678 B1 | 6/2001 | Afremov et al. | |
| 6,241,758 B1 | 6/2001 | Cox | |
| 6,242,472 B1 | 6/2001 | Sekins et al. | |
| 6,245,102 B1 | 6/2001 | Jayaraman | |
| 6,258,100 B1 * | 7/2001 | Alferness et al. | 606/108 |
| 6,264,700 B1 | 7/2001 | Kilcoyne et al. | |
| 6,267,775 B1 | 7/2001 | Clerc et al. | |
| 6,270,527 B1 | 8/2001 | Campbell et al. | |
| 6,287,290 B1 | 9/2001 | Perkins et al. | |
| 6,287,334 B1 | 9/2001 | Moll et al. | |
| 6,293,951 B1 | 9/2001 | Alferness et al. | |
| 6,299,604 B1 | 10/2001 | Ragheb et al. | |
| 6,302,893 B1 | 10/2001 | Limon et al. | |
| 6,312,407 B1 | 11/2001 | Zadno-Azizi et al. | |
| 6,325,777 B1 | 12/2001 | Zadno-Azizi et al. | |
| 6,325,778 B1 | 12/2001 | Zadno-Azizi et al. | |
| 6,327,505 B1 | 12/2001 | Medhkour et al. | |
| 6,327,772 B1 | 12/2001 | Zadno-Azizi et al. | |
| 6,328,689 B1 | 12/2001 | Gonzalez et al. | |
| 6,338,728 B1 | 1/2002 | Valerio et al. | |
| 6,350,278 B1 | 2/2002 | Lenker et al. | |
| 6,355,014 B1 | 3/2002 | Zadno-Azizi et al. | |
| 6,398,775 B1 | 6/2002 | Perkins et al. | |
| 6,402,754 B1 | 6/2002 | Gonzalez | |
| 6,416,554 B1 | 7/2002 | Alferness et al. | |
| 6,425,916 B1 | 7/2002 | Garrison et al. | |
| 6,428,561 B1 | 8/2002 | Johansson-Ruden et al. | |
| 6,439,233 B1 | 8/2002 | Geertsema | |
| 6,440,164 B1 | 8/2002 | DiMatteo et al. | |
| 6,447,530 B1 | 9/2002 | Ostrovsky et al. | |
| 6,454,754 B1 | 9/2002 | Frank | |
| 6,458,076 B1 | 10/2002 | Pruitt | |
| 6,458,153 B1 | 10/2002 | Bailey et al. | |
| 6,471,718 B1 | 10/2002 | Staehle et al. | |
| 6,471,979 B2 | 10/2002 | New et al. | |
| 6,485,407 B2 | 11/2002 | Alferness et al. | |
| 6,488,673 B1 | 12/2002 | Laufer | |
| 6,491,706 B1 | 12/2002 | Alferness et al. | |
| 6,493,589 B1 | 12/2002 | Medhkour et al. | |
| 6,503,272 B2 | 1/2003 | Duerig et al. | |
| 6,510,846 B1 | 1/2003 | O'Rourke | |
| 6,514,290 B1 | 2/2003 | Loomas | |
| 6,527,761 B1 | 3/2003 | Buch et al. | |
| 6,540,782 B1 | 4/2003 | Snyders | |
| 6,544,192 B2 | 4/2003 | Starr et al. | |
| 6,544,291 B2 | 4/2003 | Taylor | |
| 6,558,429 B2 | 5/2003 | Taylor | |
| 6,568,387 B2 | 5/2003 | Davenport et al. | |
| 6,569,166 B2 | 5/2003 | Gonzalez | |
| 6,585,639 B1 | 7/2003 | Kotmel et al. | |
| 6,589,256 B2 | 7/2003 | Forber | |
| 6,592,594 B2 | 7/2003 | Rimbaugh et al. | |
| 6,599,311 B1 | 7/2003 | Biggs et al. | |
| 6,600,307 B2 | 7/2003 | Turski | |
| 6,610,043 B1 | 8/2003 | Ingenito | |
| 6,629,951 B2 | 10/2003 | Laufer et al. | |
| 6,632,243 B1 | 10/2003 | Zadno-Azizi et al. | |
| 6,634,363 B1 | 10/2003 | Laufer et al. | |
| 6,638,285 B2 | 10/2003 | Gabbay | |
| 6,669,724 B2 | 12/2003 | Park et al. | |
| 6,673,070 B2 | 1/2004 | Edwards et al. | |
| 6,679,264 B1 | 1/2004 | Deem et al. | |
| 6,682,250 B2 | 1/2004 | Banks | |
| 6,682,520 B2 | 1/2004 | Ingenito | |
| 6,694,979 B2 * | 2/2004 | Hundertmark et al. | 128/207.14 |
| 6,709,401 B2 | 3/2004 | Soltesz et al. | |
| 6,712,812 B2 | 3/2004 | Roschak et al. | |
| 6,716,208 B2 | 4/2004 | Humes | |
| 6,722,360 B2 | 4/2004 | Doshi | |
| 6,743,259 B2 | 6/2004 | Ginn | |
| 6,746,686 B2 | 6/2004 | Hughes et al. | |
| 6,749,606 B2 | 6/2004 | Keast et al. | |
| 6,749,658 B1 | 6/2004 | DeVore et al. | |
| 6,840,952 B2 | 1/2005 | Saker et al. | |
| 6,849,049 B2 | 2/2005 | Starr et al. | |
| 6,849,084 B2 | 2/2005 | Rabkin et al. | |
| 6,860,847 B2 | 3/2005 | Alferness et al. | |
| 6,887,256 B2 | 5/2005 | Gilson | |
| 6,904,909 B2 | 6/2005 | Andreas et al. | |
| 6,911,028 B2 | 6/2005 | Shadduck | |
| 6,929,637 B2 | 8/2005 | Gonzalez et al. | |
| 6,941,950 B2 | 9/2005 | Wilson et al. | |
| 6,951,571 B1 | 10/2005 | Srivastava | |
| 6,955,675 B2 | 10/2005 | Jain | |
| 6,958,059 B2 | 10/2005 | Zadno-Azizi | |
| 6,958,076 B2 | 10/2005 | Acosta et al. | |
| 6,989,027 B2 | 1/2006 | Allen et al. | |
| 6,997,951 B2 | 2/2006 | Solem et al. | |
| 7,011,094 B2 | 3/2006 | Rapacki et al. | |
| 7,086,398 B2 | 8/2006 | Tanaka | |
| 7,100,616 B2 | 9/2006 | Springmeyer | |
| 7,141,046 B2 | 11/2006 | Perkins et al. | |
| 7,169,140 B1 | 1/2007 | Kume | |
| 7,175,644 B2 | 2/2007 | Cooper et al. | |
| 7,207,946 B2 | 4/2007 | Sirokman | |
| 7,252,086 B2 | 8/2007 | Tanaka | |
| 7,273,469 B2 | 9/2007 | Chan et al. | |
| 7,278,430 B2 | 10/2007 | Kumar | |
| 7,357,795 B2 | 4/2008 | Kaji et al. | |
| 7,412,977 B2 | 8/2008 | Fields et al. | |
| 7,422,584 B2 | 9/2008 | Loomas et al. | |
| 7,434,578 B2 | 10/2008 | Dillard et al. | |
| 7,476,203 B2 | 1/2009 | DeVore et al. | |
| 7,530,995 B2 | 5/2009 | Quijano et al. | |
| 7,533,671 B2 | 5/2009 | Gonzalez et al. | |
| 7,637,934 B2 | 12/2009 | Mangiardi et al. | |
| 7,691,151 B2 | 4/2010 | Kutsko | |
| 7,757,692 B2 | 7/2010 | Alferness et al. | |
| 7,798,974 B2 | 9/2010 | Sirokman | |
| 7,842,010 B2 | 11/2010 | Bonnette et al. | |
| 7,842,061 B2 * | 11/2010 | Dillard et al. | 606/191 |
| 7,854,228 B2 | 12/2010 | Wilson et al. | |
| 7,875,048 B2 | 1/2011 | Dillard et al. | |
| 7,887,585 B2 | 2/2011 | Gonzalez et al. | |

| | | |
|---|---|---|
| 7,896,887 B2 | 3/2011 | Rimbaugh et al. |
| 7,913,698 B2 | 3/2011 | Barry et al. |
| 7,942,931 B2 | 5/2011 | Gonzalez et al. |
| 2001/0001817 A1 | 5/2001 | Humes |
| 2001/0010017 A1 | 7/2001 | Letac et al. |
| 2001/0012949 A1 | 8/2001 | Forber |
| 2001/0025132 A1 | 9/2001 | Alferness et al. |
| 2001/0034518 A1 | 10/2001 | Edwards et al. |
| 2001/0037808 A1 | 11/2001 | Deem et al. |
| 2001/0041906 A1 | 11/2001 | Gonzalez |
| 2001/0051799 A1 | 12/2001 | Ingenito |
| 2001/0052344 A1 | 12/2001 | Doshi |
| 2001/0056274 A1 | 12/2001 | Perkins et al. |
| 2002/0007831 A1 | 1/2002 | Davenport et al. |
| 2002/0029004 A1 | 3/2002 | Starr et al. |
| 2002/0052626 A1 | 5/2002 | Gilson |
| 2002/0062120 A1 | 5/2002 | Perkins et al. |
| 2002/0072730 A1 | 6/2002 | McGill et al. |
| 2002/0077564 A1 | 6/2002 | Campbell et al. |
| 2002/0077593 A1 | 6/2002 | Perkins et al. |
| 2002/0077696 A1 | 6/2002 | Zadno-Azizi et al. |
| 2002/0087153 A1 | 7/2002 | Roschak et al. |
| 2002/0091411 A1 | 7/2002 | Saker et al. |
| 2002/0095209 A1 | 7/2002 | Zadno-Azizi et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0123749 A1 | 9/2002 | Jain |
| 2002/0138135 A1 | 9/2002 | Duerig et al. |
| 2002/0147462 A1 | 10/2002 | Mair et al. |
| 2003/0013935 A1 | 1/2003 | Alferness et al. |
| 2003/0018327 A1 | 1/2003 | Truckai et al. |
| 2003/0018344 A1 | 1/2003 | Kaji et al. |
| 2003/0024527 A1 | 2/2003 | Ginn |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0070682 A1 | 4/2003 | Wilson et al. |
| 2003/0083671 A1 | 5/2003 | Rimbaugh et al. |
| 2003/0083730 A1 | 5/2003 | Stinson |
| 2003/0109869 A1 | 6/2003 | Shadduck |
| 2003/0125763 A1 | 7/2003 | McInnes |
| 2003/0127090 A1 | 7/2003 | Gifford et al. |
| 2003/0154988 A1 | 8/2003 | DeVore |
| 2003/0158515 A1 | 8/2003 | Gonzalez et al. |
| 2003/0167065 A1 | 9/2003 | Kumar |
| 2003/0180922 A1 | 9/2003 | Eaton et al. |
| 2003/0181922 A1 | 9/2003 | Alferness |
| 2003/0183235 A1 | 10/2003 | Rimbaugh et al. |
| 2003/0195385 A1 | 10/2003 | DeVore |
| 2003/0212337 A1 | 11/2003 | Sirokman |
| 2003/0212412 A1 | 11/2003 | Dillard et al. |
| 2003/0216769 A1 | 11/2003 | Dillard et al. |
| 2003/0225445 A1 | 12/2003 | Derus et al. |
| 2003/0228344 A1 | 12/2003 | Fields et al. |
| 2004/0010209 A1 | 1/2004 | Sirokman |
| 2004/0024356 A1 | 2/2004 | Tanaka |
| 2004/0039250 A1 | 2/2004 | Tholfsen et al. |
| 2004/0039443 A1 | 2/2004 | Solem et al. |
| 2004/0040555 A1 | 3/2004 | Tanaka |
| 2004/0059263 A1 | 3/2004 | DeVore |
| 2004/0060563 A1 | 4/2004 | Rapacki et al. |
| 2004/0127912 A1 | 7/2004 | Rabkin et al. |
| 2004/0143282 A1 | 7/2004 | Dillard et al. |
| 2004/0167636 A1 | 8/2004 | Dillard et al. |
| 2004/0194780 A1 | 10/2004 | Doshi |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0210306 A1 | 10/2004 | Quijano et al. |
| 2004/0211412 A1 | 10/2004 | Alferness et al. |
| 2004/0211434 A1 | 10/2004 | Loomas et al. |
| 2004/0243140 A1 | 12/2004 | Alferness et al. |
| 2004/0244802 A1 | 12/2004 | Tanaka |
| 2005/0033310 A1 | 2/2005 | Alferness et al. |
| 2005/0033344 A1 | 2/2005 | Dillard et al. |
| 2005/0096721 A1 | 5/2005 | Mangin et al. |
| 2005/0137611 A1 | 6/2005 | Escudero et al. |
| 2005/0137714 A1 | 6/2005 | Gonzalez et al. |
| 2005/0145253 A1 | 7/2005 | Wilson et al. |
| 2005/0166925 A1 | 8/2005 | Wilson et al. |
| 2005/0222580 A1 | 10/2005 | Gifford, III et al. |
| 2005/0245894 A1 | 11/2005 | Zadno-Azizi |
| 2005/0267323 A1 | 12/2005 | Dorros et al. |
| 2006/0032497 A1 | 2/2006 | Doshi |
| 2006/0074382 A1 | 4/2006 | Gonzalez et al. |
| 2006/0155217 A1 | 7/2006 | DeVore |
| 2006/0200076 A1 | 9/2006 | Gonzalez et al. |
| 2006/0206147 A1 | 9/2006 | DeVore et al. |
| 2006/0235432 A1 | 10/2006 | DeVore |
| 2006/0235467 A1 | 10/2006 | DeVore |
| 2006/0249164 A1 | 11/2006 | Springmeyer |
| 2006/0270940 A1 | 11/2006 | Tsukashima et al. |
| 2007/0185531 A1 | 8/2007 | Rimbaugh et al. |
| 2007/0209204 A1 | 9/2007 | Chase et al. |
| 2007/0221230 A1 | 9/2007 | Thompson et al. |
| 2007/0225747 A1 | 9/2007 | Perkins et al. |
| 2007/0232992 A1 | 10/2007 | Kutsko et al. |
| 2007/0250022 A1 | 10/2007 | Sirokman |
| 2008/0015627 A1 | 1/2008 | DeVore |
| 2008/0132989 A1 | 6/2008 | Snow et al. |
| 2009/0099530 A1 | 4/2009 | Adams et al. |
| 2009/0182369 A1 | 7/2009 | Gonzalez |
| 2009/0205667 A1 | 8/2009 | Alferness et al. |
| 2009/0292262 A1 | 11/2009 | Adams et al. |
| 2010/0256714 A1 | 10/2010 | Springmeyer |
| 2010/0262071 A1 | 10/2010 | Kutsko et al. |
| 2011/0054632 A1 | 3/2011 | Alferness |
| 2011/0079221 A1 | 4/2011 | Dillard |

FOREIGN PATENT DOCUMENTS

| | | |
|---|---|---|
| CA | 2308186 | 5/1999 |
| CA | 2375752 | 1/2001 |
| CA | 2401331 | 3/2001 |
| CA | 2408923 | 11/2001 |
| CN | 101868199 | 10/2010 |
| CN | 102058443 | 5/2011 |
| DE | 100 04 979 | 8/2000 |
| EP | 0 665 029 | 8/1995 |
| EP | 0 743 071 | 11/1996 |
| EP | 1 151 729 | 11/2001 |
| EP | 1 157 663 | 11/2001 |
| EP | 1 206 276 | 5/2002 |
| EP | 1 198 269 | 10/2009 |
| EP | 03 716 212 | 12/2010 |
| GB | 2 082 071 | 3/1982 |
| GB | 2 324 729 | 11/1998 |
| GB | 2 348 138 | 9/2000 |
| JP | 58-163332 | 9/1983 |
| JP | 60-10740 | 1/1994 |
| JP | H11-513577 | 11/1999 |
| JP | 2003-503162 | 1/2003 |
| JP | 2003-533266 | 11/2003 |
| JP | 2004-535887 | 12/2004 |
| JP | 2005-527297 | 9/2005 |
| JP | 3742010 | 11/2005 |
| JP | 4387803 B2 | 10/2009 |
| JP | 2011-500171 | 1/2011 |
| RU | 2140211 | 10/1999 |
| SU | 852321 | 7/1981 |
| SU | 1371700 | 2/1988 |
| SU | 1593651 | 9/1990 |
| WO | WO 88/09683 | 12/1988 |
| WO | WO 94/26175 | 11/1994 |
| WO | WO 95/32018 | 11/1995 |
| WO | WO 96/34582 | 11/1996 |
| WO | WO 96/37167 | 11/1996 |
| WO | WO 97/09932 | 3/1997 |
| WO | WO 97/13471 | 4/1997 |
| WO | WO 97/27893 | 8/1997 |
| WO | WO 97/42871 | 11/1997 |
| WO | WO 97/44085 | 11/1997 |
| WO | WO 98/00840 | 1/1998 |
| WO | WO 98/01084 | 1/1998 |
| WO | WO 98/19633 | 5/1998 |
| WO | PCT/US98/18366 | 9/1998 |
| WO | WO 98/39047 | 9/1998 |
| WO | WO 98/44854 | 10/1998 |

| | | |
|---|---|---|
| WO | PCT/GB98/652 | 11/1998 |
| WO | WO 98/48706 | 11/1998 |
| WO | WO 99/01076 | 1/1999 |
| WO | WO 99/13801 | 3/1999 |
| WO | WO 99/26692 | 6/1999 |
| WO | WO 99/32040 | 7/1999 |
| WO | WO 99/42059 | 8/1999 |
| WO | WO 99/42161 | 8/1999 |
| WO | WO 99/59503 | 11/1999 |
| WO | WO 99/64109 | 12/1999 |
| WO | WO 00/18329 | 4/2000 |
| WO | WO 00/27292 | 5/2000 |
| WO | WO 00/42950 | 7/2000 |
| WO | WO 00/51500 | 9/2000 |
| WO | WO 00/51510 | 9/2000 |
| WO | WO 00/62699 | 10/2000 |
| WO | WO 00/78386 | 12/2000 |
| WO | WO 00/78407 | 12/2000 |
| WO | PCT/US00/18286 | 1/2001 |
| WO | WO 01/02042 | 1/2001 |
| WO | WO 01/03641 | 1/2001 |
| WO | WO 01/03642 | 1/2001 |
| WO | WO 01/05334 | 1/2001 |
| WO | WO 01/10313 | 2/2001 |
| WO | WO 01/10314 | 2/2001 |
| WO | WO 01/12104 | 2/2001 |
| WO | WO 01/13839 | 3/2001 |
| WO | WO 01/13908 | 3/2001 |
| WO | WO 01/28433 | 4/2001 |
| WO | WO 01/30266 | 5/2001 |
| WO | WO 01/37897 | 5/2001 |
| WO | WO 01/45590 | 6/2001 |
| WO | WO 01/49213 | 7/2001 |
| WO | WO 01/52775 | 7/2001 |
| WO | WO 01/54585 | 8/2001 |
| WO | WO 01/54625 | 8/2001 |
| WO | WO 01/54685 | 8/2001 |
| WO | PCT/US01/6958 | 9/2001 |
| WO | WO 01/66190 | 9/2001 |
| WO | WO01/66190 | 9/2001 |
| WO | WO 01/70114 | 9/2001 |
| WO | WO 01/74271 | 10/2001 |
| WO | PCT/NZ01/00092 | 11/2001 |
| WO | WO 01/87170 | 11/2001 |
| WO | WO 01/89366 | 11/2001 |
| WO | WO 01/95786 | 12/2001 |
| WO | WO 02/05884 | 1/2002 |
| WO | PCT/US01/28360 | 3/2002 |
| WO | WO 02/22072 | 3/2002 |
| WO | WO 02/32333 | 4/2002 |
| WO | WO 02/34322 | 5/2002 |
| WO | WO 02/38038 | 5/2002 |
| WO | WO 02/47575 | 6/2002 |
| WO | WO 02/056794 | 7/2002 |
| WO | WO 02/064045 | 8/2002 |
| WO | WO 02/064190 | 8/2002 |
| WO | WO 02/069823 | 9/2002 |
| WO | WO 02/094087 | 11/2002 |
| WO | WO 01/95786 | 12/2002 |
| WO | WO 03/022124 | 3/2003 |
| WO | WO 03/030975 | 4/2003 |
| WO | WO 03/034927 | 5/2003 |
| WO | WO 03/034946 | 5/2003 |
| WO | WO 03/041779 | 5/2003 |
| WO | WO 03/047468 | 6/2003 |
| WO | WO 03/078579 | 9/2003 |
| WO | WO 03/079944 | 10/2003 |
| WO | WO 03/088820 | 10/2003 |
| WO | WO 03/094996 | 11/2003 |
| WO | WO 03/099164 | 12/2003 |
| WO | WO 2004/010845 | 5/2004 |
| WO | WO 2004/080347 | 9/2004 |
| WO | WO 2005/013835 | 2/2005 |
| WO | WO 2007/123690 | 11/2007 |
| WO | WO 2009/049261 | 4/2009 |
| WO | WO 2009/135070 | 11/2009 |
| WO | WO 2010/118056 | 10/2010 |

OTHER PUBLICATIONS

European Supplemental Search Report dated Nov. 9, 2009 for EP Application No. 03 71 0804 in 2 pgs.

Canadian Office Action dated Nov. 5, 2009, re Application No. 2,484,086 in 2 pgs.

U.S. Appl. No. 09/686,204, filed Oct. 10, 2000, and its ongoing prosecution history including without limitation Office Actions, Amendments, Remarks, and any other potentially relevant documents.

U.S. Appl. No. 09/379,972, filed Aug. 24, 1999, Pub. No. 2010/0256714, published Oct. 7, 2010 and its ongoing prosecution history including without limitation Office Actions, Amendments, Remarks, and any other potentially relevant documents.

U.S. Appl. No. 10/052,875, filed Oct. 25, 2001, Pub. No. 2003/0083671, published May 1, 2003, and its ongoing prosecution history including without limitation Office Actions, Amendments, Remarks, and any other potentially relevant documents.

U.S. Appl. No. 09/881,862, filed Jun. 14, 2001, Pub. No. 2001/0052344, published Dec. 20, 2001 and its ongoing prosecution history including without limitation Office Actions, Amendments, Remarks, and any other potentially relevant documents.

U.S. Appl. No. 10/091,712, filed Mar. 6, 2002, Pub. No. 2002/0112729, published Aug. 22, 2002, and its ongoing prosecution history including without limitation Office Actions, Amendments, Remarks, and any other potentially relevant documents.

U.S. Appl. No. 10/317,667, filed Dec. 11, 2002, Pub. No. 2003/0158515, published Aug. 21, 2003, and its ongoing prosecution history including without limitation Office Actions, Amendments, Remarks, and any other potentially relevant douments.

U.S. Appl. No. 10/409,785, filed Apr. 8, 2003, and its ongoing prosecution history including without limitation Office Actions, Amendments, Remarks, and any other potentially relevant documents.

U.S. Appl. No. 10/259,007, filed Sep. 26, 2002, Pub. No. 2003/0212337, published Nov. 13, 2003, and its ongoing prosecution history including without limitation Office Actions, Amendments, Remarks, and any other potentially relevant documents.

U.S. Appl. No. 10/744,577, filed Dec. 22, 2003, Pub. No. 2004/0167636, published Aug. 26, 2004, and its ongoing prosecution history including without limitation Office Actions, Amendments, Remarks, and any other potentially relevant documents.

U.S. Appl. No. 11/260,012, filed Oct. 26, 2005, Pub. No. 2006/0155217, published Jul. 13, 2006, and its ongoing prosecution history including without limitation Office Actions, Amendments, Remarks, and any other potentially relevant documents.

U.S. Appl. No. 10/745,401, filed Dec. 22, 2003, Pub. No. 2005/0137714, published Jun. 23, 2005, and its ongoing prosecution history including without limitation Office Actions, Amendments, Remarks, and any other potentially relevant documents.

U.S. Appl. No. 11/585,415, filed Oct. 24, 2006, Pub. No. 2007/0232992, published Oct. 4, 2007, and its ongoing prosecution history including without limitation Office Actions, Amendments, Remarks, and any other potentially relevant documents.

U.S. Appl. No. 12/428,287, filed Apr. 22, 2009, Pub. No. 2009/0205667, published Aug. 20, 2009, and its ongoing prosecution history including without limitation Office Actions, Amendments, Remarks, and any other potentially relevant documents.

U.S. Appl. No. 11/738,412, filed Apr. 20, 2007, Pub. No. 2009/0250022, published on Oct. 25, 2007, and its ongoing prosecution history including without limitation Office Actions, Amendments, Remarks, and any other potentially relevant documents.

U.S. Appl. No. 10/746,981, filed Dec. 23, 2003, Pub. No. 2004/0143282, published Jul. 22, 2004, and its ongoing prosecution history including without limitation Office Actions, Amendments, Remarks, and any other potentially relevant documents.

U.S. Appl. No. 10/933,778, filed Sep. 3, 2004, Pub. No. 2005/0033344, published Feb. 10, 2005, and its ongoing prosecution history including without limitation Office Actions, Amendments, Remarks, and any other potentially relevant documents.

U.S. Appl. No. 12/398,122, filed Mar. 4, 2009, Pub. No. 2009/0182369, published Jul. 16, 2009, and its ongoing prosecution history including without limitation Office Actions, Amendments, Remarks, and any other potentially relevant documents.

U.S. Appl. No. 11/733,710, filed Apr. 10, 2007, Pub. No. 2007/0185531, published Aug. 9, 2007, and its ongoing prosecution history including without limitation Office Actions, Amendments, Remarks, and any other potentially relevant documents.

U.S. Appl. No. 10/150,547, filed May 17, 2002, and its ongoing prosecution history including without limitation Office Actions, Amendments, Remarks, and any other potentially relevant documents.

U.S. Appl. No. 10/178,073, filed Jun. 21, 2001, and its ongoing prosecution history including without limitation Office Actions, Amendments, Remarks, and any other potentially relevant documents.

U.S. Appl. No. 09/951,105, filed Sep. 11, 2001, and its ongoing prosecution history including without limitation Office Actions, Amendments, Remarks, and any other potentially relevant documents.

U.S. Appl. No. 10/178,073, filed Jun. 21, 2002, and its ongoing prosecution history including without limitation Office Actions, Amendments, Remarks, and any other potentially relevant documents.

U.S. Appl. No. 10/103,487, filed Mar. 20, 2002, and its ongoing prosecution history including without limitation Office Actions, Amendments, Remarks, and any other potentially relevant documents.

U.S. Appl. No. 10/418,929, filed Apr. 17, 2003, and its ongoing prosecution history including without limitation Office Actions, Amendments, Remarks, and any other potentially relevant documents.

U.S. Appl. No. 10/124,790, filed Apr. 16, 2002, and its ongoing prosecution history including without limitation Office Actions, Amendments, Remarks, and any other potentially relevant documents.

U.S. Appl. No. 10/143,353, filed May 9, 2002, and its ongoing prosecution history including without limitation Office Actions, Amendments, Remarks, and any other potentially relevant documents.

U.S. Appl. No. 10/196,513, filed Jul. 15, 2002, and its ongoing prosecution history including without limitation Office Actions, Amendments, Remarks, and any other potentially relevant documents.

U.S. Appl. No. 10/254,392, filed Sep. 24, 2002, and its ongoing prosecution history including without limitation Office Actions, Amendments, Remarks, and any other potentially relevant documents.

U.S. Appl. No. 10/827,384, filed Apr. 19, 2004, and its ongoing prosecution history including without limitation Office Actions, Amendments, Remarks, and any other potentially relevant documents.

U.S. Appl. No. 10/847,554, filed May 17, 2004, and its ongoing prosecution history including without limitation Office Actions, Amendments, Remarks, and any other potentially relevant documents.

U.S. Appl. No. 10/387,963, filed Mar. 12, 2003, and its ongoing prosecution history including without limitation Office Actions, Amendments, Remarks, and any other potentially relevant documents.

U.S. Appl. No. 10/847,427, filed May 17, 2004, and its ongoing prosecution history including without limitation Office Actions, Amendments, Remarks, and any other potentially relevant documents.

U.S. Appl. No. 10/48,041, filed May 18, 2004, and its ongoing prosecution history including without limitation Office Actions, Amendments, Remarks, and any other potentially relevant documents.

U.S. Appl. No. 10/848,571, filed Feb. 10, 2005, and its ongoing prosecution history including without limitation Office Actions, Amendments, Remarks, and any other potentially relevant documents.

U.S. Appl. No. 11/178,640, filed Jul. 11, 2005, and its ongoing prosecution history including without limitation Office Actions, Amendments, Remarks, and any other potentially relevant documents.

U.S. Appl. No. 11/204,383, filed Aug. 15, 2005, and its ongoing prosecution history including without limitation Office Actions, Amendments, Remarks, and any other potentially relevant documents.

U.S. Appl. No. 11/417,738, May 3, 2006, and its ongoing prosecution history including without limitation Office Actions, Amendments, Remarks, and any other potentially relevant documents.

U.S. Appl. No. 11/418,541, filed May 3, 2006, and its ongoing prosecution history including without limitation Office Actions, Amendments, Remarks, and any other potentially relevant documents.

U.S. Appl. No. 11/417,553, filed May 3, 2006, and its ongoing prosecution history including without limitation Office Actions, Amendments, Remarks, and any other potentially relevant documents.

U.S. Appl. No. 11/416,337, filed May 2, 2006, and its ongoing prosecution history including without limitation Office Actions, Amendments, Remarks, and any other potentially relevant documents.

U.S. Appl. No. 11/417,944, filed May 3, 2006, and its ongoing prosecution history including without limitation Office Actions, Amendments, Remarks, and any other potentially relevant documents.

U.S. Appl. No. 11/781,130, filed Jul. 20, 2007, and its ongoing prosecution history including without limitation Office Actions, Amendments, Remarks, and any other potentially relevant documents.

U.S. Appl. No. 12/249,243, filed Oct. 10, 2008, and its ongoing prosecution history including without limitation Office Actions, Amendments, Remarks, and any other potentially relevant documents.

U.S. Appl. No. 12/422,179, filed Apr. 10, 2009, and its ongoing prosecution history including without limitation Office Actions, Amendments, Remarks, and any other potentially relevant documents.

U.S. Appl. No. 12/721,426, filed Mar. 10, 2010, and its ongoing prosecution history including without limitation Office Actions, Amendments, Remarks, and any other potentially relevant documents.

U.S. Appl. No. 12/754,394, filed Apr. 5, 2010, and its ongoing prosecution history including without limitation Office Actions, Amendments, Remarks, and any other potentially relevant documents.

U.S. Appl. No. 21/828,629, filed Jul. 1, 2010, and its ongoing prosecution history including without limitation Office Actions, Amendments, Remarks, and any other potentially relevant documents.

Chest Drains, from webmaster@atroi.ed/cp., from website Mar. 21, 2002; pp. 1-3.

Chest Drains, from webmaster@surgical-tutor.orq.uk; from Website on Mar. 21, 2002; pp. 1-3.

EDO Certamics Products and Services, from webmaster@edocorp.com; from website on Mar. 21, 2002; pp. 1,2.

Exploring Chest Drain Options; from webmaster google.com; RNWeb: Continuing Education; from website on Mar. 21, 2002; pp. 1-6.

Marco: Bubble Detector, from webmaster@marco.de, from Website on Mar. 21, 2002; pp. 1-3.

Oasis Dry Suction Chest Drains; Instructions for Use; Atrium Medical Corporation, Hudson New Hampshire, on Mar. 27, 2002,pp. 1-4.

SIII Control and Display Modules; from webmaster@stoeckert.de; from website on Mar. 21, 2002, pp. 15.

Tube Thorascostomy; from webmaster@merck.com/pubs/mmanual; from Website Mar. 21, 2003, pp. 1,2.

Understanding Chest Drainage; from webmaster@nursingceu.com; from website on Mar. 21, 2002; pp. 1-15.

Amendment mailed Mar. 3, 2004 in response to Office Action dated Oct. 3, 2003 in the related copending U.S. Appl. No. 09/951,105.

Andre A. Kulisz, Autocath 100—Nonsurgical, Intraurethral Bladder Control Device for Urinary Incontinent and Urinary Retentive Women—Another Dr. Kulisz's Development, http://www.kulisz.com/autocath.htm, 2003, 3 pp.

Dillard et al.,"Evaluation of a Nvel Intra-bronchial Valve Device to Produce Lung Volume Reduction," Poster show at conference in Jun. 2002.

Ellis, James H., Balloon Catheter Occlusion of Bronchopleural Fistulae, May 7, 1981, AJR: 138, Jan. 1982, p. 157-159.

EWS Endobronchial Watanabe Spigots, Novatech, edited Apr. 17, 2002.

European Supplemental Search Report in European Appln. No. 00969008.2, dated Feb. 26, 2004, 5 pp.
International Search Report in International application No. PCT/US00/40701, mailed Jan. 25, 2001, 3 pp.
European Search Report in European Appln. No. 02759335.9, dated Jan. 31, 2007.
International Search Report in International application No. PCT/US02/25555, mailed Mar. 19, 2003, 4 pp.
International Search Report and Written Opinion for Application No. PCT/US2004/025458 mailed Nov. 30, 2004.
Extended European Search Report for EP 08 0205468, dated Jul. 28, 2009.
Harris et al., "The Experimental Production in Dogs of Emphysema with Associated Asthatic Syndrome by Means of an Interatracheal Ball Valve," J Exp Med 30:1919; 75-88.
Horiuchi et al: Three Cases of Intractable Pneumothorax Treated Sucessfully by Bronchial Embolization using Silicon; JJSB, 2001. pp. 25-30.
Inaspettato: Endoscopic Treatment of Bronchopleural Fistulas Using N-butyl-2-cyanoacrylate; Surgical Laparoscopy & Endoscopy; vol. 4 No. 1, pp. 62-64, 1994.
Jones et al: Closure of a Benign Broncho-Oesophageal Fistula by Endoscopic Injection of Bovine Collagen, Cyanocrylate Glue and Gelfoam; 1996, pp. 53-55 Aust. N. Z. J.. Surg.
Lewis et al, "Pulmonary Interstitial Emphysema: Selective Bronchial Occlusion with a Swan-Ganz Catheter." Archives of Disease in Childhood, 63:1988, 313-315.
Matthew et al. "Selective Bronchial Obstruction for Treatment of Bullous Interstitial Emphysema," J. of Ped. 96:1980, 475-477.
Office Action mailed Oct. 3, 2003 from related copending U.S. Appl. No. 09/951,105.
Office Action dated Apr. 28, 2009 for Canadian Application No. 2,459,702.
Okada et al: Emergent Bronchofiberoptic Bronchial Occlusion for Intractable Pneumothorax with Severe Emphysema; The Japanese Journal of Thoracic and Cardiovascular Surgery, 1998. pp. 1078-1081.
PCT Search Report and Written Opinion from corresponding PCT Application No. PCT/US2004/007721, Sep. 23, 2004.
PCT International Search Report from corresponding PCT Application No. PCT/US2007/007923, dated May 20, 2008 in 2 pages.
Preliminary and Written Report from corresponding PCT Application No. PCT/US2007/007923, dated Sep. 30, 2008 in 7 pages.
Puhakka et al., "Acute Bronchial Obstruction: An Experimental Rabbit Model Study." Int. J. of Pediatric Otorhinolaryngology. 18:1989, 107-118.
Snider et al., "The Definition of Emphysema: Report of the National Heart Lung and Blood Institute, Division of Lung Diseases Workshop", Am. Ev. Respir. Dis., 132:182-185, 1985.
Watanabe et al: Bronchial Embolization Using Dental Impression Material in a Case of Pyelo-bronchial Fistula with Candida Fungemia; 1991. Journal of the Japan Society for Bronchology, pp. 607-610.
Australian Office Action of Oct. 29, 2007, Application No. 2003219927.
European. Supplemental Search Report of Feb. 28, 2008, Application No. 03 716 212.0-1265.
European Office Action of Dec. 23, 2008, Application No. 03 716 212.0-1265.
European Office Action of Jun. 17, 2009, Application No. 03 716 212.0 -1265.
International Search Report of Jul. 7, 2003, Application No. PCT/US03/05968.
Japanese Office Action of Feb. 3, 2009, Application No. 2003-577779.
Office Action of Oct. 20, 2004, U.S. Appl. No. 10/103,487, filed Mar. 3, 2002.
Office Action of Jun. 14, 2005, U.S. Appl. No. 10/103,487, filed Mar. 3, 2002.
Office Action of Feb. 8, 2006, U.S. Appl. No. 10/103,487, filed Mar. 3, 2002.
Office Action of May 19, 2006, U.S. Appl. No. 10/103,487, filed Mar. 3, 2002.
Office Action of Sep. 12, 2006, U.S. Appl. No. 10/103,487, filed Mar. 3, 2002.
Office Action of Mar. 22, 2007, U.S. Appl. No. 10/103,487, filed Mar. 3, 2002.
European Office Action of Dec. 8, 2010, Application No. 09739872.1.
European Office Action on May 6, 2011, Application No. 09739872.1.
Canadian Office Action dated Dec. 14, 2010 for Canadian Application No. 2,459,702.
Canadian Office Action dated Mar. 9, 2010 for Canadian Application No. 2,459,702.
Chinese Office Action dated Jun. 4, 2010 re CN Application No. 200780019455.6.
European Examination Report dated Apr. 14, 2010 for EP Application No. 03 71 0804.
European Office Action of Apr. 28, 2011, Application No. 10196887.3-1269.
International Preliminary Report on Patentability for Application No. PCT/US2010/030131, dated Mar. 18, 2011.
International Report on Patentability dated Dec. 23, 2009 re PCT/US2008/079650.
International Search Report and Written Opinion for Application No. PCT/US2010/030131, dated Jun. 18, 2010.
International Search Report dated 10/01/03 re PCT Application No. PCT/US2003/14868.
International Search Report dated Jan. 30, 2009 re PCT/US2008/079650.
PCT Search Report and Written Opinion from corresponding PCT Application No. PCT/US2004/007721 dated Mar. 12, 2004.
Russian Office Action, for App. No. 2008139081/14(050381), dated Nov. 24, 2010.
US Office Action mailed Oct. 3, 2003 from related copending U.S. Appl. No. 09/951,105.
US Office Action of Dec. 10, 2010, U.S. Appl. No. 11/880,090, filed Jul. 19, 2007.

* cited by examiner

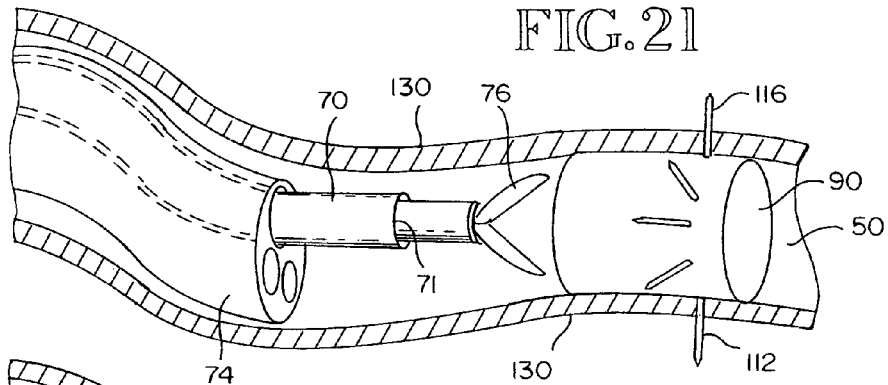
FIG. 21
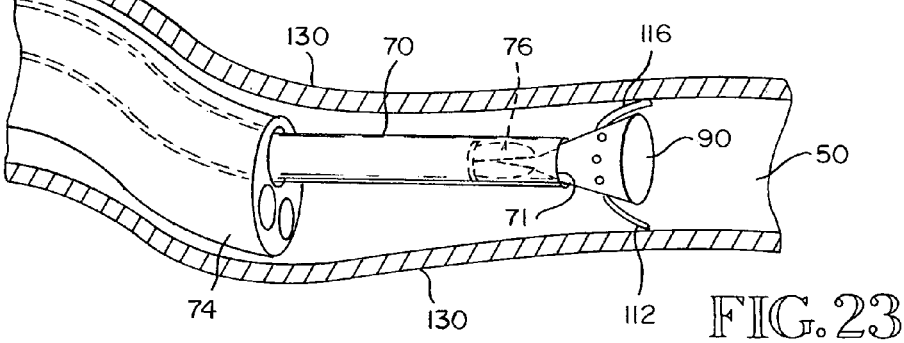
FIG. 22
FIG. 23
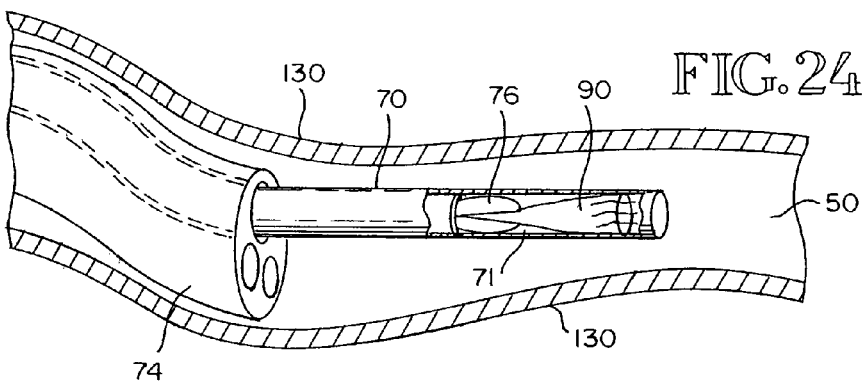
FIG. 24

REMOVABLE ANCHORED LUNG VOLUME REDUCTION DEVICES AND METHODS

CROSS-REFERENCE TO RELATED APPLICATIONS

This application is a continuation of U.S. patent application Ser. No. 10/103,487, filed Mar. 20, 2002, and is now abandoned, which is hereby incorporated in its entirety.

BACKGROUND OF THE INVENTION

1. Field of the Invention

The present invention is generally directed to a removable anchored device, system, and method for treating Chronic Obstructive Pulmonary Disease (COPD). The present invention is more particularly directed to providing an anchored intra-bronchial obstruction that may be removable.

2. Description of the Related Art

COPD has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

The incidence, prevalence, and health-related costs of COPD are on the rise. Mortality due to COPD is also on the rise. In 1991, COPD was the fourth leading cause of death in the United States and had increased 33% since 1979. COPD affects the patient's whole life. It has three main symptoms: cough; breathlessness; and wheeze. At first, breathlessness may be noticed when running for a bus, digging in the garden, or walking uphill. Later, it may be noticed when simply walking in the kitchen. Over time, it may occur with less and less effort until it is present all of the time. COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Pharmacotherapy may include bronchodilator therapy to open up the airways as much as possible or inhaled betaagonists. For those patients who respond poorly to the foregoing or who have persistent symptoms, ipratropium bromide may be indicated. Further, courses of steroids, such as corticosteroids, may be required. Lastly, antibiotics may be required to prevent infections and influenza and pneumococcal vaccines may be routinely administered. Unfortunately, there is no evidence that early, regular use of pharmacotherapy will alter the progression of COPD.

About 40 years ago, it was first postulated that the tethering force that tends to keep the intrathoracic airways open was lost in emphysema and that by surgically removing the most affected parts of the lungs, the force could be partially restored. Although the surgery was deemed promising, the lung volume reduction surgery (LVRS) procedure was abandoned. LVRS was later revived. In the early 1990's, hundreds of patients underwent the procedure. However, the procedure has fallen out of favor when Medicare stopping reimbursing for LVRS. Unfortunately, data is relatively scarce and many factors conspire to make what data exists difficult to interpret. The procedure is currently under review in a controlled clinical trial. However, what data does exist tends to indicate that patients benefited from the procedure in terms of an increase in forced expiratory volume, a decrease in total lung capacity, and a significant improvement in lung function, dyspnea, and quality of life. Improvements in pulmonary function after LVRS have been attributed to at least four possible mechanisms. These include enhanced elastic recoil, correction of ventilation/perfusion mismatch, improved efficiency of respiratory muscaulature, and improved right ventricular filling.

Lastly, lung transplantation is also an option. Today, COPD is the most common diagnosis for which lung transplantation is considered. Unfortunately, this consideration is given for only those with advanced COPD. Given the limited availability of donor organs, lung transplant is far from being available to all patients.

There is a need for additional non-surgical options for permanently treating COPD without surgery. A promising new therapy includes non-surgical apparatus and procedures for lung volume reduction by permanently obstructing the air passageway that communicates with the portion of the lung to be collapsed. The therapy includes placing an obstruction in the air passageway that prevents inhaled air from flowing into the portion of the lung to be collapsed. Lung volume reduction with concomitant improved pulmonary function may be obtained without the need for surgery. The effectiveness of obstructions may be enhanced if it is anchored in place. The effectiveness may also be enhanced if the obstruction is removable. However, no readily available apparatus and method exists for anchoring the obstruction, and for removal if required.

In view of the foregoing, there is a need in the art for a new and improved apparatus and method for permanently obstructing an air passageway that is anchored in place, and that may be removed if required. The present invention is directed to a device, system, and method that provide such an improved apparatus and method for treating COPD.

SUMMARY OF THE INVENTION

The present invention provides an anchored intrabronchial device for placement in an air passageway of a patient to collapse a lung portion associated with the air passageway. The device includes an obstructing member that prevents air from being inhaled into the lung portion to collapse the lung portion, and an anchor that anchors the obstruction device within the air passageway when the anchor is deployed. The anchor may engage the air passageway wall, and may pierce into the air passageway wall. The obstructing member and the anchor may be simultaneously deployable. The anchor may be releasable from the air passageway for removal of the obstructing member. A portion of the intra-bronchial device may be collapsible. The anchor may be releasable from the air passageway for removal of the obstructing member by collapsing a portion of the obstructing member, or by drawing the obstructing member proximally. The anchor may include a resilient material for imparting a force against the air passageway to deform the air passageway to more positively anchor the obstructing member. The anchor may comprise material having memory of an original shape, and resiliency to return the material to that shape. The obstructing member may comprise material having memory of an original shape, and resiliency to return the material to that shape. The obstructing member may be a one-way valve.

In another embodiment of the present invention, a method of reducing the size of a lung by collapsing a portion of the lung is provided. The method includes the step of providing an intra-bronchial device comprising an obstructing member which is so dimensioned when deployed in an air passageway communicating with the portion of the lung to be collapsed to preclude air from being inhaled, and an anchor that anchors the obstructing member when the anchor is deployed. The method further includes the steps of placing the obstructing member in the air passageway, and deploying the anchor. The anchor may be releasable for removal of the obstructing member. The obstructing member may form a one-way valve. A portion of the obstructing member may be collapsible.

In a further embodiment of the present invention, a method of reducing the size of a lung by collapsing a portion of the lung with a removable device is provided. The method includes the step of providing an intra-bronchial device and an obstructing member that is so dimensioned when deployed in an air passageway communicating with the portion of the lung to be collapsed to preclude air from being inhaled, and an anchor that anchors the obstructing member when the anchor is deployed. The method includes the additional steps of placing the obstructing member in the air passageway, deploying an anchor, and removing the obstructing member. The anchor is releasable from the air passageway for removal of the intra-bronchial device, and the step of removing the obstructing member includes the further step of releasing the anchor. The obstructing member may form a one-way valve. At least a portion of the obstructing member may be collapsible, and the step of removing the obstructing member includes the further step of collapsing a portion of the obstructing member.

In yet another embodiment of the present invention, an air passageway-obstructing device is provided. The obstructing device includes obstructing means for obstructing air flow within the air passageway, and anchoring means to anchor the air passageway obstructing device within the air passageway.

In yet a further embodiment of the present invention, an air passageway-obstructing device is provided that includes obstructing means for obstructing air flow within the air passageway, and anchoring means to anchor the air passageway obstructing device within the air passageway, the anchoring means being releasable for removal of the obstructing means from the air passageway.

These and various other features as well as advantages which characterize the present invention will be apparent from a reading of the following detailed description and a review of the associated drawings.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify like elements, and wherein:

FIG. 21 is a side view of an initial step in removing the device of FIG. 18 from an air passageway;

FIG. 22 is a side view of an intermediate step in removing the device of FIG. 18 from an air passageway;

FIG. 23 is a side view of another intermediate step in removing the device of FIG. 18 from an air passageway;

FIG. 24 is a side view illustrating the collapse of the device of FIG. 18 during its removal from an air passageway;

DETAILED DESCRIPTION OF THE PREFERRED EMBODIMENT

Figure 1:
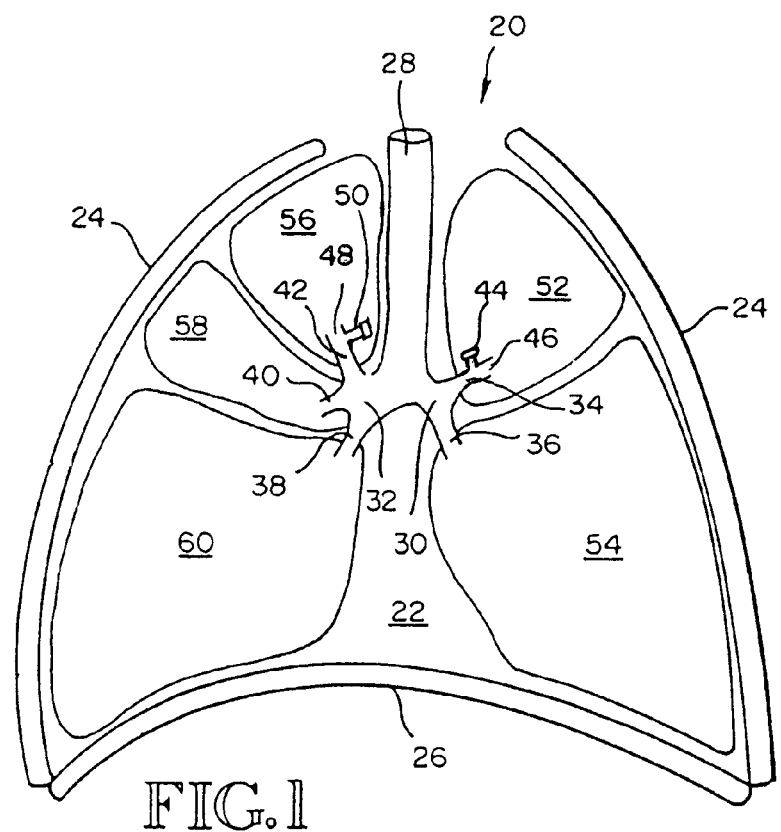
FIG. 1 is a simplified sectional view of a thorax illustrating a healthy respiratory system.

In the following detailed description of exemplary embodiments of the invention, reference is made to the accompanying drawings that form a part hereof. The detailed description and the drawings illustrate how specific exemplary embodiments by which the invention may be practiced. These embodiments are described in sufficient detail to enable those skilled in the art to practice the invention. It is understood that other embodiments may be utilized, and other changes may be made, without departing from the spirit or scope of the present invention. The following detailed description is therefore not to be taken in a limiting sense, and the scope of the present invention is defined by the appended claims.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

Additionally, throughout the specification, claims, and drawings, the term "proximal" means nearest the trachea, and "distal" means nearest the bronchioles.

Briefly stated, an aspect of the invention provides an anchored intra-bronchial device for placement in an air passageway of a patient to collapse a lung portion associated with the air passageway. A further aspect of the invention provides removability of the intra-bronchial device, either by releasing the anchors for removal of the entire device or by separating the obstructing member and removing it.

FIG. 1 is a sectional view of a healthy respiratory system. The respiratory system 20 resides within the thorax 22 that occupies a space defined by the chest wall 24 and the diaphragm 26.

The respiratory system 20 includes the trachea 28, the left mainstem bronchus 30, the right mainstem bronchus 32, the bronchial branches 34, 36, 38, 40, and 42 and sub-branches 44, 46, 48, and 50. The respiratory system 20 further includes left lung lobes 52 and 54 and right lung lobes 56, 58, and 60. Each bronchial branch and sub-branch communicates with a respective different portion of a lung lobe, either the entire lung lobe or a portion thereof. As used herein, the term "air passageway" is meant to denote either a bronchi or bronchiole, and typically means a bronchial branch or sub-branch which communicates with a corresponding individual lung lobe or lung lobe portion to provide inhaled air thereto or conduct exhaled air therefrom.

Characteristic of a healthy respiratory system is the arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes to fill with air. When the individual exhales, the diaphragm returns to its original arched condition to decrease the volume of the thorax. The decreased volume of the thorax causes a positive pressure within the thorax which in turn causes exhalation of the lung lobes.

Figure 2:
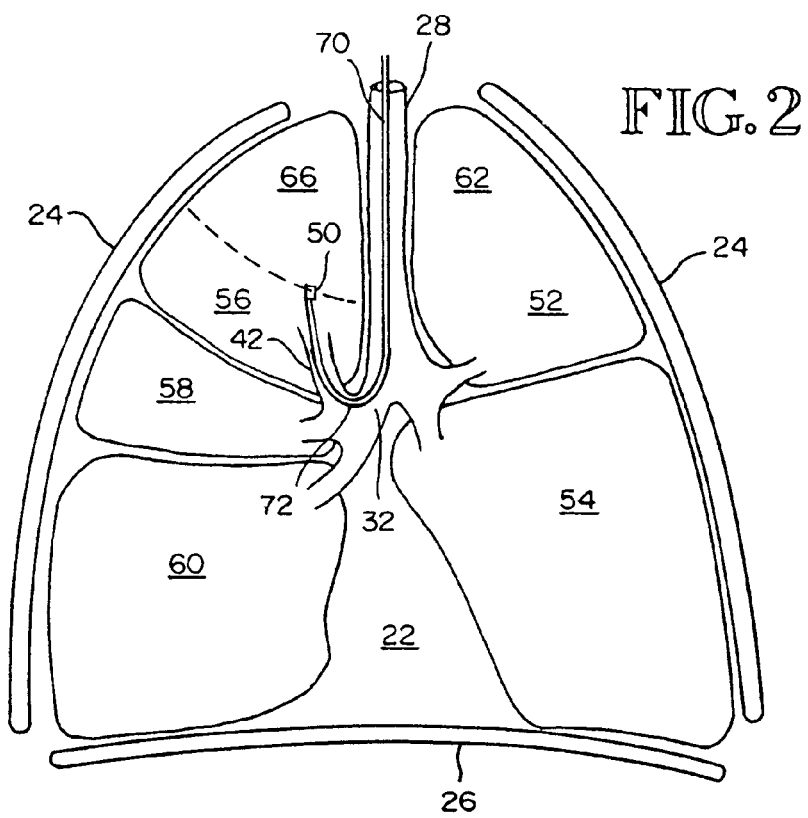
FIG. 2 is a sectional view similar to FIG. 1, but illustrating a respiratory system suffering from COPD and the execution of a first step in treating the COPD condition by reducing the size of a lung portion in accordance with the present invention.

In contrast to the healthy respiratory system of FIG. 1, FIG. 2 illustrates a respiratory system suffering from COPD. Here it may be seen that the lung lobes 52, 54, 56, 58, and 60 are enlarged and that the diaphragm 26 is not arched but substantially straight. Hence, this individual is incapable of breathing normally by moving diaphragm 28. Instead, in order to create the negative pressure in thorax 22 required for breathing, this individual must move the chest wall outwardly to increase the volume of the thorax. This results in inefficient breathing causing these individuals to breathe rapidly with shallow breaths.

It has been found that the apex portions 62 and 66 of the upper lung lobes 52 and 56, respectively, are most affected by COPD. Hence, bronchial sub-branch obstructing devices are generally employed for treating the apex 66 of the right, upper lung lobe 56. However, as will be appreciated by those skilled in the art, the present invention may be applied to any lung portion without departing from the present invention. As will be further appreciated by those skilled the in art, the present invention may be used with any type of obstructing member to provide an anchored obstructing device, which may be removed. The inventions disclosed and claimed in U.S. Pat. Nos. 6,258,100 and 6,293,951, both of which are incorporated herein by reference, provide an improved therapy for treating COPD by obstructing an air passageway using an intra-bronchial valve or plug. The present invention may be used with the apparatus, system, and methods of these patents as will be briefly described in conjunction with the disclosure of the preferred embodiments of the present invention.

The insertion of an obstructing member treats COPD by deriving the benefits of lung volume reduction surgery without the need of performing the surgery. The treatment contemplates permanent collapse of a lung portion. This leaves extra volume within the thorax for the diaphragm to assume its arched state for acting upon the remaining healthier lung tissue. As previously mentioned, this should result in improved pulmonary function due to enhanced elastic recoil, correction of ventilation/perfusion mismatch, improved efficiency of respiratory musculature, and improved right ventricle filling. The present invention supports the use of intra-bronchial plugs to treat COPD by anchoring the obstruction device in the air passageway. The present invention further supports the use of intra-bronchial plugs by providing for their removal if necessary. Use of anchors can allow the obstructing member to be relatively loosely fitted against the air passageway wall, which may provide increased mucociliary transport of mucus and debris out of the collapsed lung portion.

FIG. 2 also illustrates a step in COPD treatment using an obstructing member. Treatment is initiated by feeding a conduit or catheter 70 down the trachea 28, into the right mainstem bronchus 32, into the bronchial branch 42 and into and terminating within the sub-branch 50. The sub-branch 50 is the air passageway that communicates with the lung portion 66 to be treated, and is also referred to herein as air passageway 50. The catheter 70 is preferably formed of flexible material such as polyethylene. Also, the catheter 70 is preferably preformed with a bend 72 to assist the feeding of the catheter from the right mainstem bronchus 32 into the bronchial branch 42.

Figure 3:
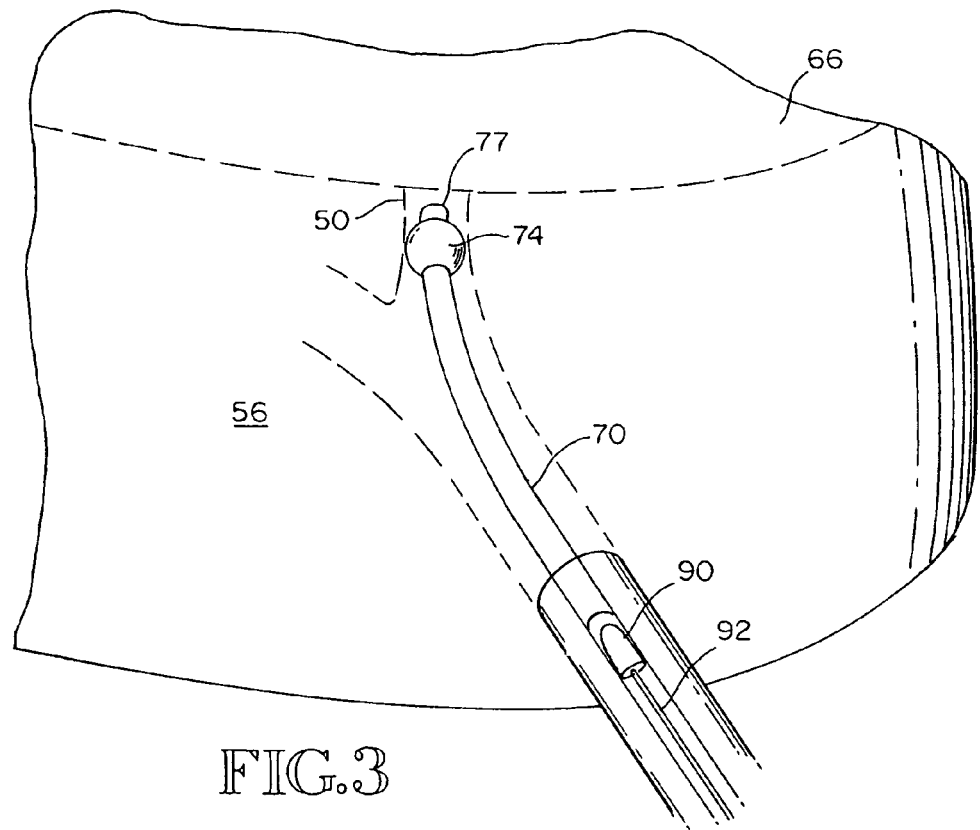
FIG. 3 is perspective view, partially in section, and to an enlarged scale, illustrating an intermediate step in the treatment.

FIG. 3 illustrates a further step in a method for placing an obstructing member 90 in a bronchial sub-branch using a catheter. The invention disclosed herein is not limited to use with the particular method illustrated herein. Catheter 70 includes an optional inflatable sealing member 74 for use with a vacuum to collapse lung portion 66 prior to insertion of obstructing member 90. The obstructing member 90 may be formed of resilient or collapsible material to enable the obstructing member 90 to be fed through the catheter 70 in a collapsed state. The obstructing member 90 and its anchors (not shown) are collapsed and fed into the catheter 70. The stylet 92 is used to push the obstructing member 90 to the end 77 of the catheter 70 for placing the obstructing member 90 within the air passageway 50 adjacent to the lung portion 66 to be permanently collapsed. Optional sealing member 74 is withdrawn after obstructing member 90 is inserted.

A function of the intra-bronchial device disclosed and claimed in this specification, including the detailed description and the claims, is described in terms of collapsing a lung portion associated with an air passageway. In some lungs, a portion of a lung may receive air from collateral air passageways. Obstructing one of the collateral air passageways may reduce the volume of the lung portion associated with the air passageway, but not completely collapse the lung portion as that term may be generally understood. As used herein, the meaning of "collapse" includes both a complete collapse of a lung portion and a partial collapse of a lung portion.

Once deployed, the obstructing member precludes inhaled air from entering the lung portion to be collapsed. In accordance with the present invention, it is preferable that the obstructing member takes the form of a one-way valve. In addition to precluding inhaled air from entering the lung portion, the member further allows air within the lung portion to be exhaled. This results in more rapid collapse of the lung portion. In addition, anchoring obstructing members that preclude both inhaled and exhaled airflow are contemplated as within the scope of the invention.

Figure 4:
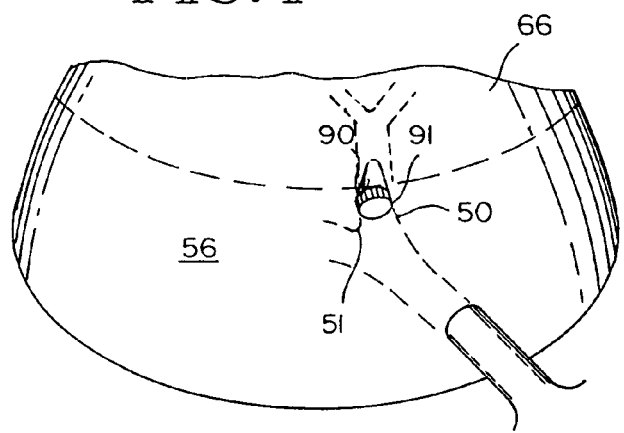
FIG. 4 is a perspective view of a conduit that may 10 be utilized in practicing the present invention.

FIG. 4 illustrates the obstructing device in place within air passageway 50. Obstructing member 90 has expanded upon placement in the air passageway 50 to seal the air passageway 50. This causes the lung portion 66 to be maintained in a permanently collapsed state. The obstructing member 90 may be any shape suitable for accomplishing its purpose, and may be a solid material or a membrane.

More specifically, the obstructing member 90 has an outer dimension 91, and when expanded, enables a contact zone with the air passageway inner dimension 51. This seals the air passageway upon placement of the obstructing member 90 in the air passageway 50 for maintaining the lung portion 66 in the collapsed state.

Alternatively, the lung portion 66 may be collapsed using vacuum prior to placement of obstructing member 90, or sealing the air passageway 50 with obstructing member 90 may collapse it. Over time, the air within the lung portion 66 will be absorbed by the body and result in the collapse of lung portion 66. Alternatively, obstructing member 90 may include the function of a one-way valve that allows air to escape from lung portion 66. Lung portion 66 will then collapse, and the valve will prevent air from being inhaled.

Figure 5:
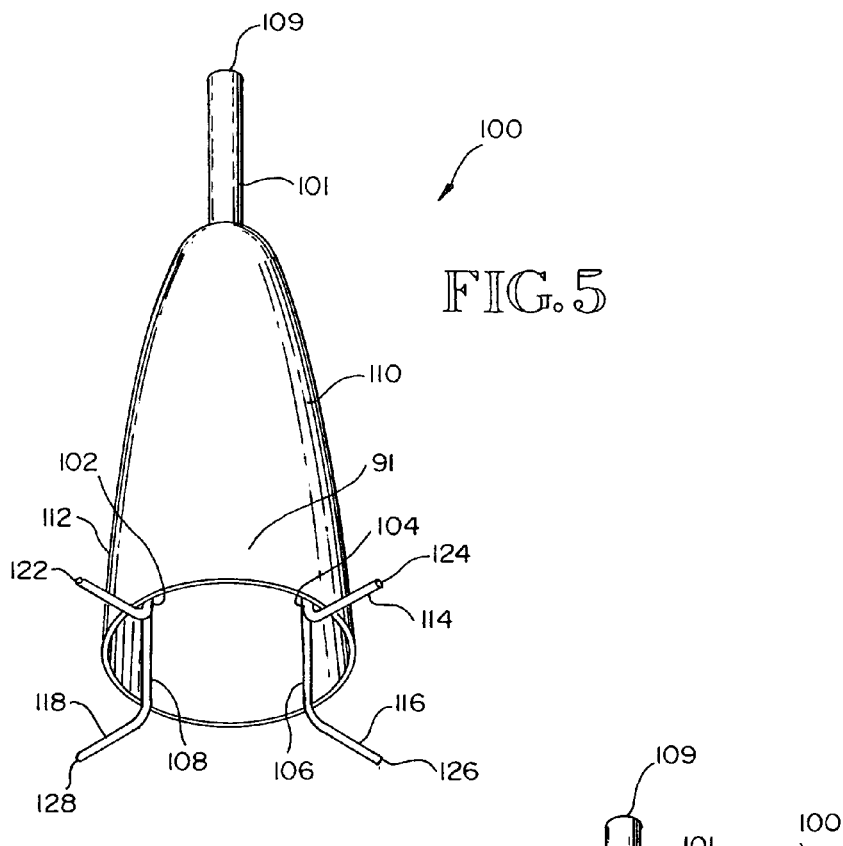
FIG. 5 is a perspective view of an intra-bronchial device, with anchors located proximally on peripheral portions of the support members, as the device would appear when fully deployed in an air passageway in accordance with the present invention.

FIG. 5 is a perspective view of an intra-bronchial device, with anchors located proximally on peripheral portions of the support members, as the device would appear when fully deployed in an air passageway in accordance with the present invention. Intra-bronchial device 100 includes a support structure 101, a central support structure 109; support members 102, 104, 106, and 108; anchors 112, 114, 116, and 118; anchor ends 122, 124, 126, and 128; and an obstructing member 110.

The support structure 101 of intra-bronchial device includes central support structure 109, and support members 102, 104, 106, and 108. The support members 102, 104, 106, and 108, carry anchors 112, 114, 116, and 118; and anchor ends 122, 124, 126, and 128, respectively. Central support structure 109 is a tubular member, preferably hypodermic needle tubing. Support members 102, 104, 106, and 108, are coupled mechanically to central support structure 109, such as by crimping, or by other methods such as adhesive or welding. Support members 102, 104, 106, and 108 are generally similar to each other. The support members are preferably formed of stainless steel, Nitinol, or other suitable material having a memory of its original shape, and resiliency to return the material to that shape.

Anchors 112, 114, 116, and 118 are extensions of support members 102, 104, 106, and 108. The anchors are formed by bending the support members to an angle that will result in a deployed anchor engaging the air passageway wall by piercing it approximately perpendicularly. In this preferred embodiment, the bend angle is approximately a right angle. Anchor ends 122, 124, 126, and 128 may be shaped to promote piercing the air passageway wall.

Obstructing member 110 is carried on the support structure 101, and includes a flexible membrane open in the proximal direction and which may be formed of silicone or polyurethane, for example. The obstructing member 110 is secured to the central support structure 109, and may be additionally secured to the support members at its larger diameter 91. It may be secured by adhesive, or other manner known in the art. Obstructing member 110 may be loosely carried on support members 102, 104, 106, and 108, such that it expands on inhalation to form a seal against a wall of the air passageway, and contracts on exhalation to allow air and mucociliary transport from the collapsed lung. This provides a one-way valve function.

Figure 6:
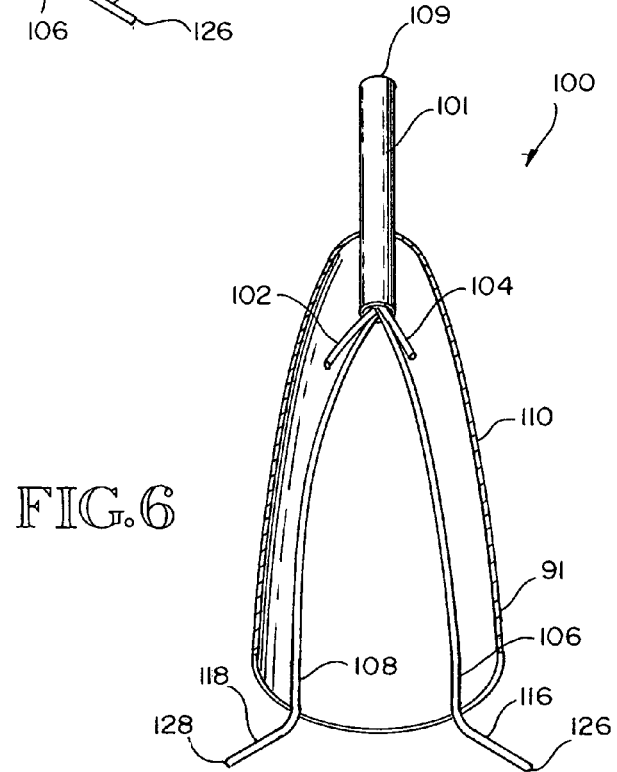
FIG. 6 is a partial section view of the device of FIG. 5 showing additional details of the support structure.

FIG. 6 is a partial section view of the device of FIG. 5 showing additional detail of the support structure. The linear cross-section view of FIG. 6 exposes the arrangement of support members 106 and 108 in their deployed configuration.

The details of support members 102 and 104 are omitted from FIG. 6 for clarity, but are the same as support members 106 and 108. The distal end of obstructing member 110 is carried on central support structure 109. Support members 106 and 108 are shown emanating from central support structure 109, and arranged to loosely support to obstructing member 110 at its larger diameter 91. This allows obstructing member 110 to expand on inhalation and seal at the contact zone 129, and to partially contract on exhalation to allow exhalation of air and mucociliary transport.

In an alternative embodiment, support members 106 and 108 do not actively support obstructing member 110, and the expansion and contraction of obstructing member 110 is governed by its elasticity.

Figure 7:
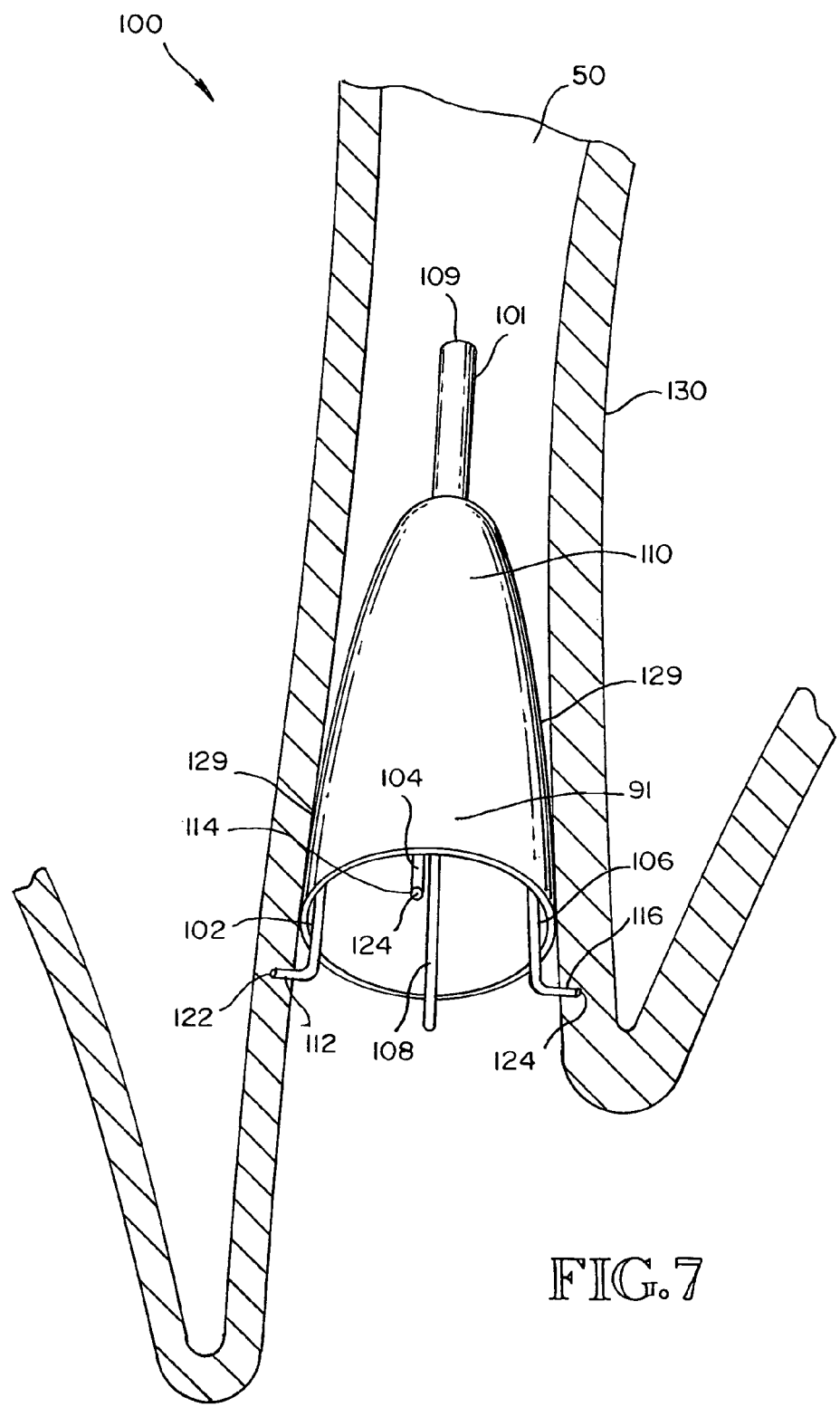
FIG. 7 is a perspective view of the intra-bronchial device of FIG. 5 anchored in an air passageway.

FIG. 7 is a perspective view of the intra-bronchial device of FIG. 5 anchored in an air passageway. Intra-bronchial device 100 is illustrated with anchors 112 and 116 piercing into the air passageway wall 130 of air passageway 50. This anchors the intra-bronchial device 100 in place.

Intra-bronchial device 100 is collapsible for insertion into an internal lumen of a catheter. At least the support members 102, 104, 106, and 108, and the obstructing member 110, may be collapsed. Intra-bronchial device 100 is inserted into the catheter lumen, which is typically already placed in the air passageway 50 as generally illustrated in FIG. 3. Using the stylet, intra-bronchial device 100 is advanced down the catheter lumen into the air passageway 50 to where the device is to be deployed. Once the point of deployment is reached, intra-bronchial device 100 is expelled from the catheter and assumes its deployed shape as illustrated in FIG. 5. Upon deployment, obstructing member 110 expands to form a contact zone 129 with the wall 130 of the air passageway 50 to prevent air from being inhaled into the lung portion to collapse the lung portion. Simultaneously upon deployment, the memory and resiliency of the support members 102, 104, 106, and 108 impart a force on the anchor ends 122, 124, 126, and 128, and urge the anchors 112, 114, 116, and 118 to engage air passageway wall 130 by piercing. The anchors pierce into and become embedded in the wall 130 of the air passageway 50, preferably without projecting through the wall 130. Stops may be incorporated into the anchors to limit piercing of the wall 130.

For example, the bend between the support member and the anchor may form a stop.

The preclusion of air from being inhaled into the lung portion may be terminated by eliminating the obstructing effect of intra-bronchial device 100. The preclusion of air by the embodiment illustrated in FIGS. 5-7 may be eliminated by releasing anchors 112, 114, 116, and 118 from the air passageway wall 130. The anchors may be released by inserting a catheter into air passageway 50 in proximity to intra-bronchial device 100. A retractor device, such as biopsy forceps, capable of gripping a portion of intra-bronchial device 100 is inserted in the catheter. The forceps are used to engage a portion of the support structure 101 of intra-bronchial device 100, and draw it toward the catheter. The drawing action releases anchors 112, 114, 116, and 118 from air passageway wall 130. The intrabronchial device 110 is then drawn into the catheter with the forceps, causing the support structure 101 and obstructing member 110 to collapse. The collapsed device 100 now fully enters the catheter lumen for removal from the patient. Alternatively, the obstructing effect may be eliminated by grabbing the obstructing member 110, releasing it from the support structure 101, and removing obstructing member 110 from the patient.

Figure 8:
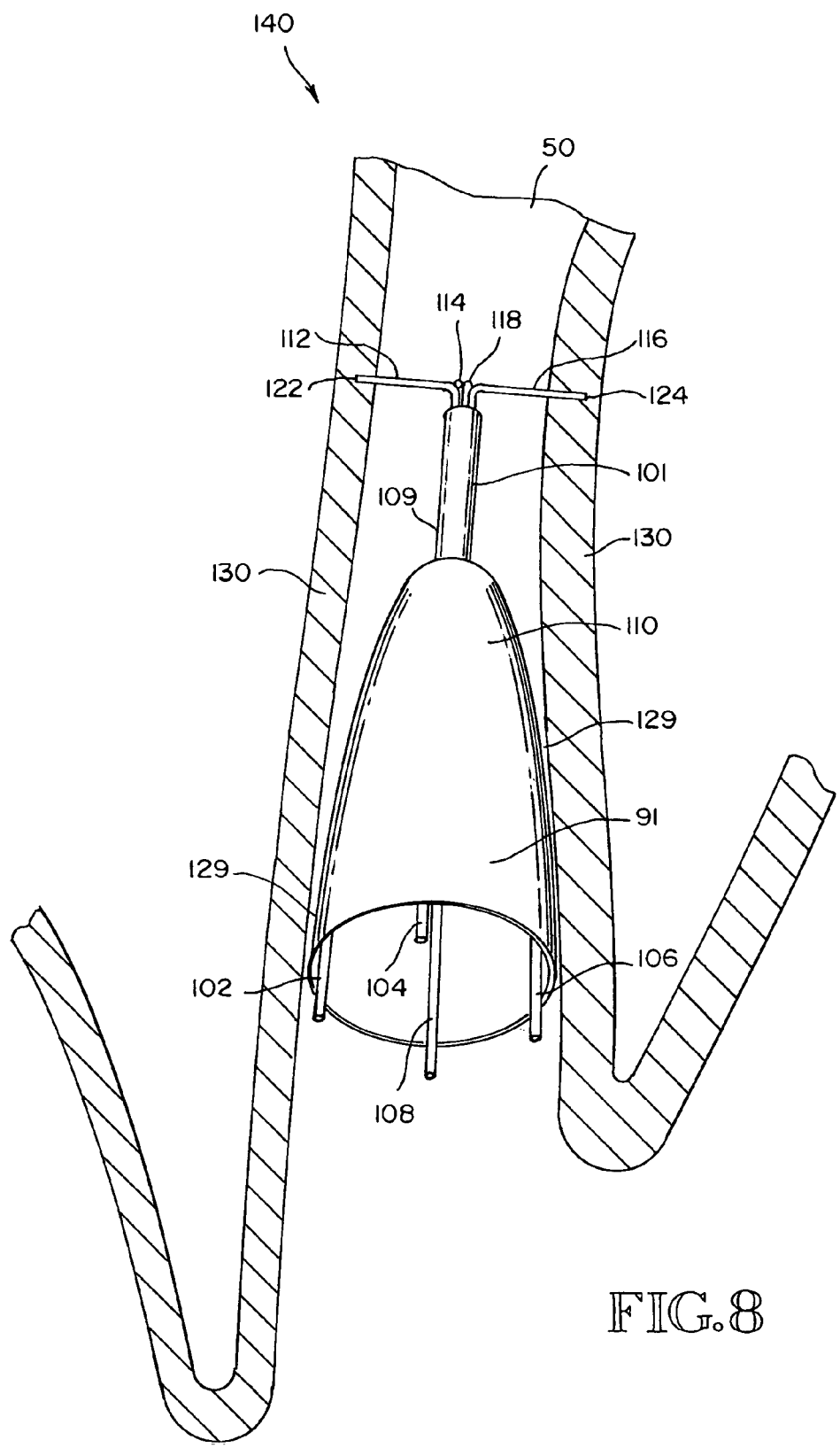
FIG. 8 illustrates an intra-bronchial device, with anchors carried distally on the central support structure, fully deployed in an air passageway in accordance with an alternative embodiment of the invention.

FIG. 8 illustrates an intra-bronchial device, with anchors carried distally on the central support structure, fully deployed in an air passageway in accordance with an alternative embodiment of the invention. The anchors 112, 114, 116, and 118 of intra-bronchial device 140 are carried on portions of support members 102, 104, 106, and 108 distal of the central support structure 109. The support members are gathered together and carried by the central support structure 109. Other than the anchors 112, 114, 116, and 118 being formed and carried on distal portions of support members 102, 104, 106, and 108, intra-bronchial device 140 is substantially similar in construction, operation, and removal as the intra-bronchial device 100 of FIG. 5.

When intra-bronchial device 140 is compressed for insertion into the catheter lumen for placement in the air passageway, the anchors, 112, 114, 116, and 118 are collapsed into a first configuration. In the first configuration, the anchor ends 122, 124, 126, and 128 are moved toward obstructing member 110, and anchors 112, 114, 116, and 118 thereby folded toward obstructing member 110. When intra-bronchial device 100 is deployed from the catheter lumen, the memory and resiliency of the support members 102, 104, 106, and 108 impart a force that moves the anchors 112, 114, 116, and 118 into a second configuration to engage air passageway wall 130. This is the deployed configuration illustrated in FIG. 8. For removal, drawing intra-bronchial device 140 toward the catheter causes the anchor ends 122, 124, 126, and 128 to move away from obstructing member 110 to a third configuration. Anchors 112, 114, 116, and 118 are thereby folded away from obstructing member 110 and are released from engagement with air passageway wall 130 for removal of the intra-bronchial device 140. In an alternative embodiment, the anchors 112, 114, 116, and 118 may be formed on additional support members carried by central support structure 109, instead of being formed from distal portions of support members 102, 104, 106, and 108.

Figure 9:
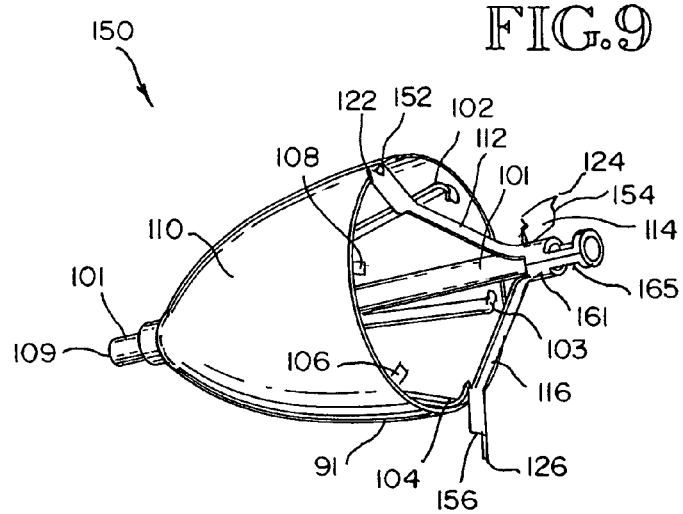
FIG. 9 is a perspective view of an intra-bronchial device, with proximal anchors carried on the central support structure, in accordance with an alternative embodiment of the invention.
Figure 10:
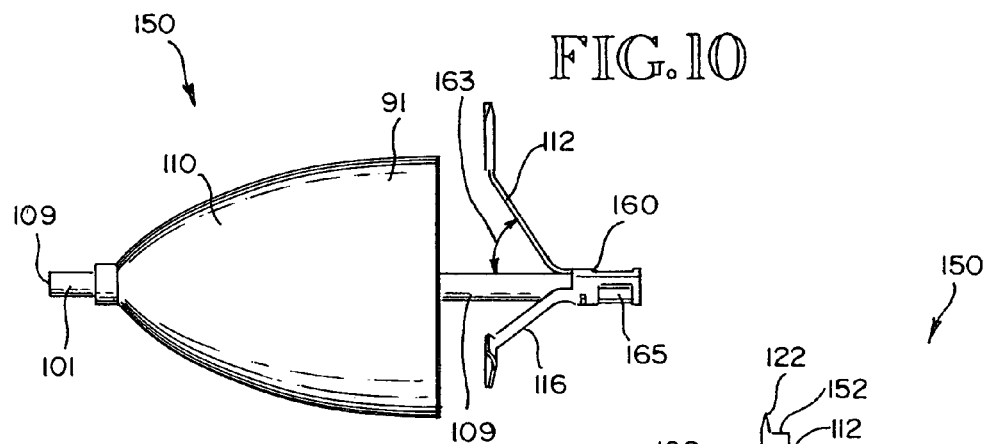
FIG. 10 is a side view of an intra-bronchial device, with proximal anchors carried on the central support structure, in accordance with an alternative embodiment of the invention.
Figure 11:
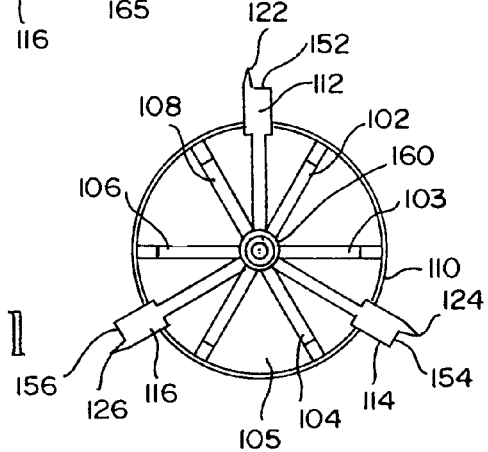
FIG. 11 is an end view of an intra-bronchial device, with proximal anchors carried on the central support structure, in accordance with an alternative embodiment of the invention.

FIGS. 9-11 illustrate an intra-bronchial device, with proximal anchors carried on the central support structure, in accordance with an alternative embodiment of the invention.

FIG. 9 is a perspective view, FIG. 10 is a side view, and FIG. 11 is an end view of the device. Intra-bronchial device 150 is generally similar in construction, operation, placement, and removal to the intra-bronchial device 100 of FIG. 5. Its structure has six support members and three anchors, with anchor stops. Anchors 112, 114, and 116 include stops 152, 154, and 156, respectively. Intra-bronchial device 150 also includes an anchor base 160, an anchor base aperture 165, anchor base angle 163, and additional support members 103 and 105.

Central support structure 109 extends both proximal and distal of obstructing member 110, and carries anchor base 161 proximal of obstructing member 110, carries anchors 112, 114, and 116, and includes anchor base aperture 165. The linear plane of anchors 112, 114, and 116 intersect anchor base 161 at anchor base angle 163. Anchor base angle 163 is selected to optimize anchor deployment force and anchor release. Stops 152, 154, and 156 include a flat area to limit the piercing of the air passageway wall by anchor ends 122, 124, and 126. In alternative embodiments, the stops can be any configuration or shape known to those skilled in the art to limit the piercing.

In operation, when intra-bronchial device 150 is compressed for insertion into the catheter lumen for placement in the air passageway, anchors 112, 114, and 116 are collapsed into a first configuration. In the first configuration, the anchor ends 122, 124, and 126 are moved toward obstructing member 110, thereby decreasing anchor base angle 163 and folding anchors 112, 114, and 116 toward obstructing member 110. The anchor ends and the anchors may be moved by sliding a catheter or hollow member over anchor base 161 and toward obstructing member 110. When intra-bronchial device 150 is deployed from the catheter lumen, the memory and resiliency of the anchors 112, 114, and 116, anchor angle 163, and anchor base 161 impart a force that moves the anchor members into a second configuration, which is the deployed configuration, to engage air passageway wall 130. The second or deployed configuration is illustrated in FIGS. 9-11. Stops 152, 154, and 156 limit the piercing of the air passageway wall by anchor ends 122, 124, and 126.

For removal, a retractor device is deployed from a catheter to engage anchor base 161 and restrain intra-bronchial device 150. The retractor device may be a biopsy forceps to engage anchor base 161, or a hooked device to engage anchor base aperture 165. A catheter is then moved distally over anchor base 161, and in contact with anchors 112, 114, and 116. The catheter is further moved against anchors 112, 114, and 116, while intra-bronchial device 150 is restrained at anchor base 161. This releases the anchors 112, 114, and 116 from the air passageway wall. This collapses the anchors into to the first configuration for removal. Intra-bronchial device 150 is then further drawn into the catheter by pulling on the retractor device used to engage anchor base 161. This collapses support structure 101 and obstructing member 110 so that they may be fully drawn into the catheter. Once drawn into the catheter, intra-bronchial device 160 may be removed from the air passageway and the patient.

Figure 12:
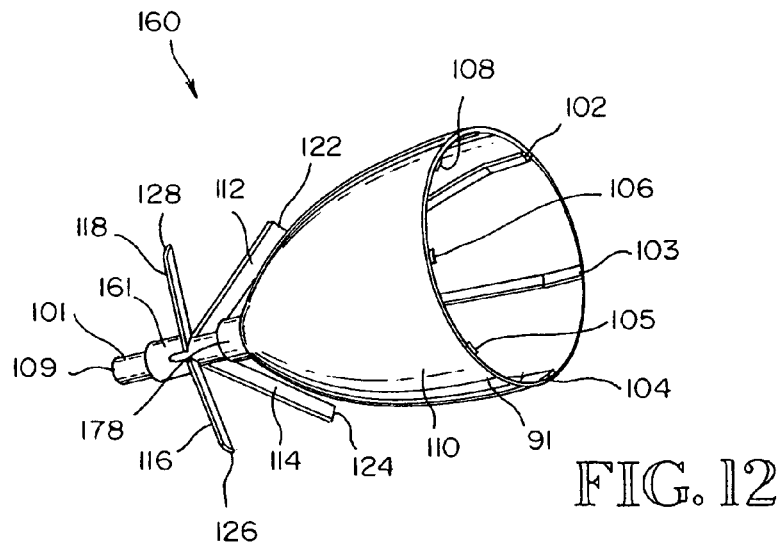
FIG. 12 is a perspective view of an intra-bronchial device, with distal friction anchors carried on the central support structure, in accordance with an alternative embodiment of the invention.
Figure 13:
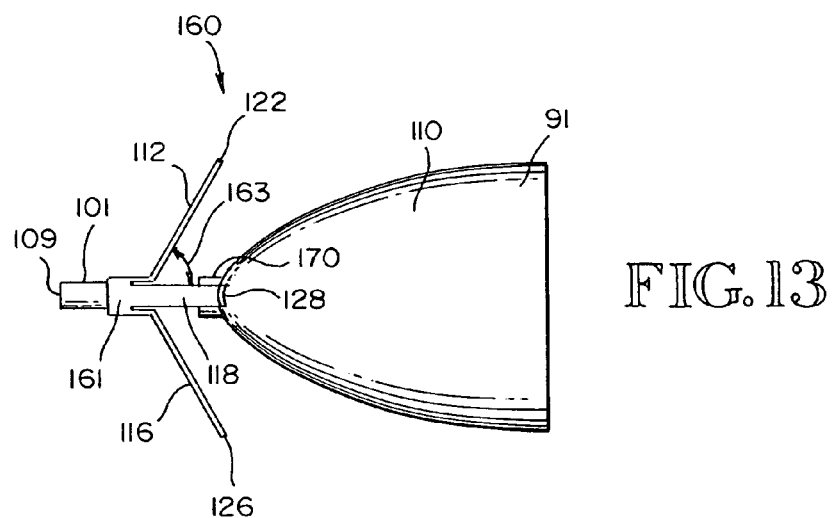
FIG. 13 is a side view of an intra-bronchial device, with distal friction anchors carried on the central support structure, in accordance with an alternative embodiment of the invention.
Figure 14:
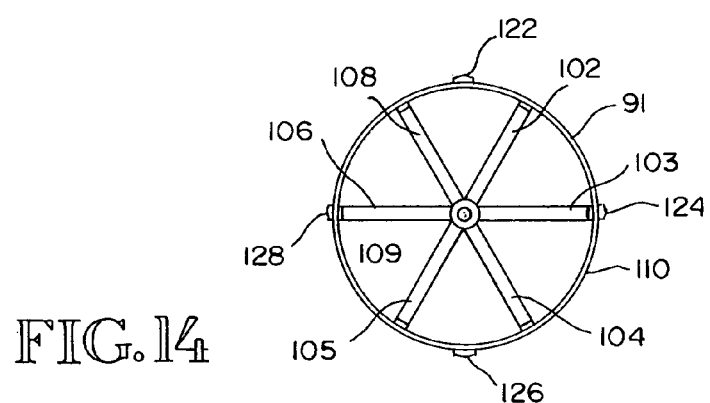
FIG. 14 is an end view of an intra-bronchial device, with distal friction anchors carried on the central support structure, in accordance with an alternative embodiment of the invention.

FIGS. 12-14 illustrate an intra-bronchial device, with distal friction anchors carried on the central support structure, in accordance with an alternative embodiment of the invention.

FIG. 12 is a perspective view, FIG. 13 is a side view, and FIG. 14 is an end view. Intra-bronchial device 160 is generally similar in construction, placement, and operation to the intra-bronchial device 150 of FIGS. 9-11. Intra-bronchial device 160 is removed in the manner described in conjunction with FIG. 7. However, Intra-bronchial device 160 differs from intra-bronchial device 150 in that the structure includes four distal anchors with anchor ends 122, 124, 126, and 128 shaped into pads that deform and frictionally engage the air passageway wall to more positively anchor intra-bronchial device 160 without piercing. The structure also includes an obstructing member support base 170.

Central support structure 109 extends distal of obstructing member 110, and carries anchor base 161 distal of obstructing member 110. Anchor base 161 carries anchors 112, 114, 116, and 118. The linear plane of anchors 112, 114, 116, and 118 intersects anchor base 161 at anchor angle 163. Anchor angle 163 is selected to optimize anchor deployment force and anchor release. The anchors 112, 114, 116, and 118, and anchor base 161 may be constructed by laser cutting a single piece of hypodermic tubing lengthwise to form the anchors 112, 114, 116, and 118, and then bending the anchors to form anchor angle 163. Anchor base 161 is secured to central support structure 109. Support members 102, 103, 104, 105, 106, and 108, and the obstructing member support member base 170 may be constructed in a like manner. Obstructing member 110 is secured to the obstructing member support base 170, and alternatively to support members 102, 103, 104, 105, 106, and 108. The assembly of obstructing member 110 and support base 170 is secured to central support structure 109. Central support structure 109 may extend proximal of support member base 170 to provide a surface for gripping the intra-bronchial device 160 for removal, and may include an aperture to be engaged by a hooked device.

Figure 15:
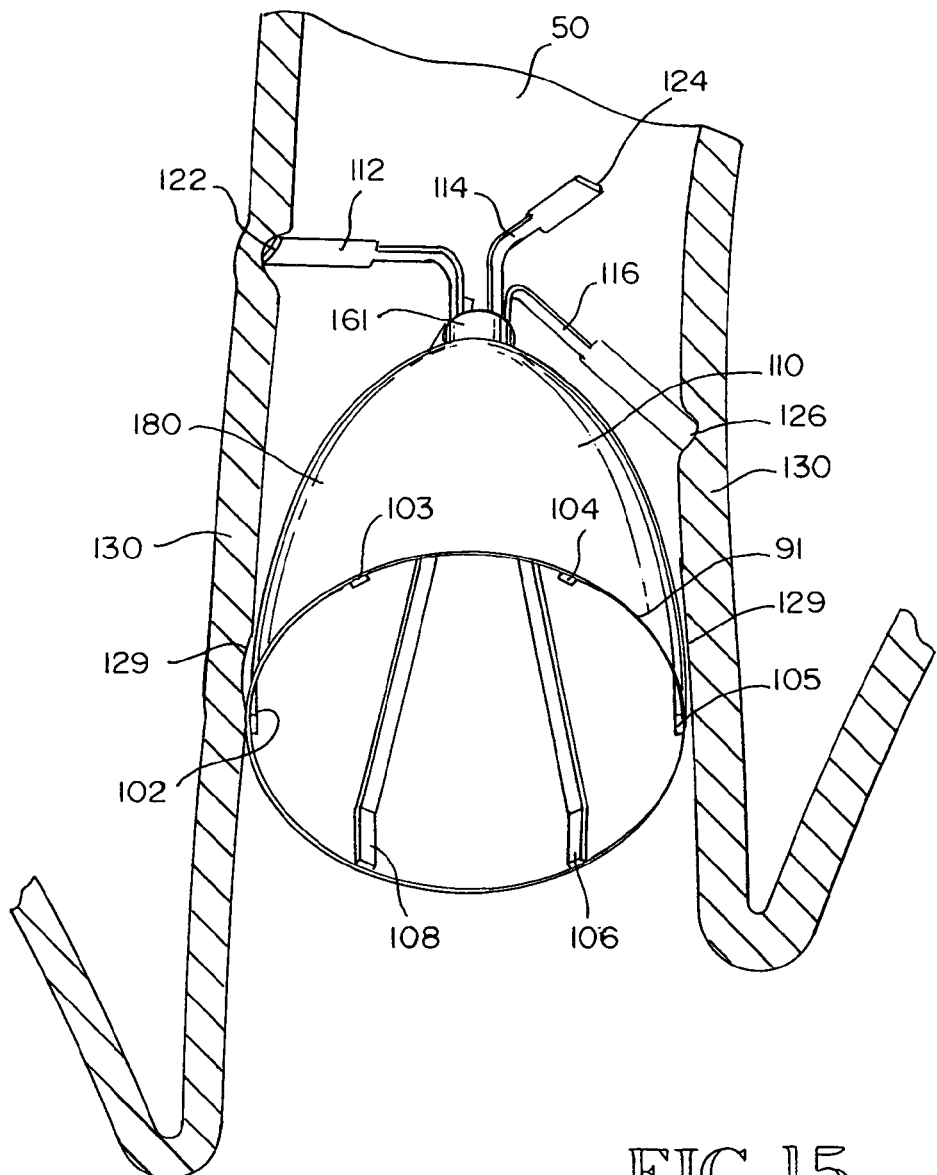
FIG. 15 is a perspective view an intra-bronchial device similar to that of FIGS. 12-14 anchored in an air passageway.

FIG. 15 is a perspective view an intra-bronchial device similar to that of FIGS. 12-14 anchored in an air passageway. It illustrates pad-shaped anchor ends 122-128 of intra-bronchial device 180 deforming and frictionally engaging air passageway wall 130.

Figure 16:
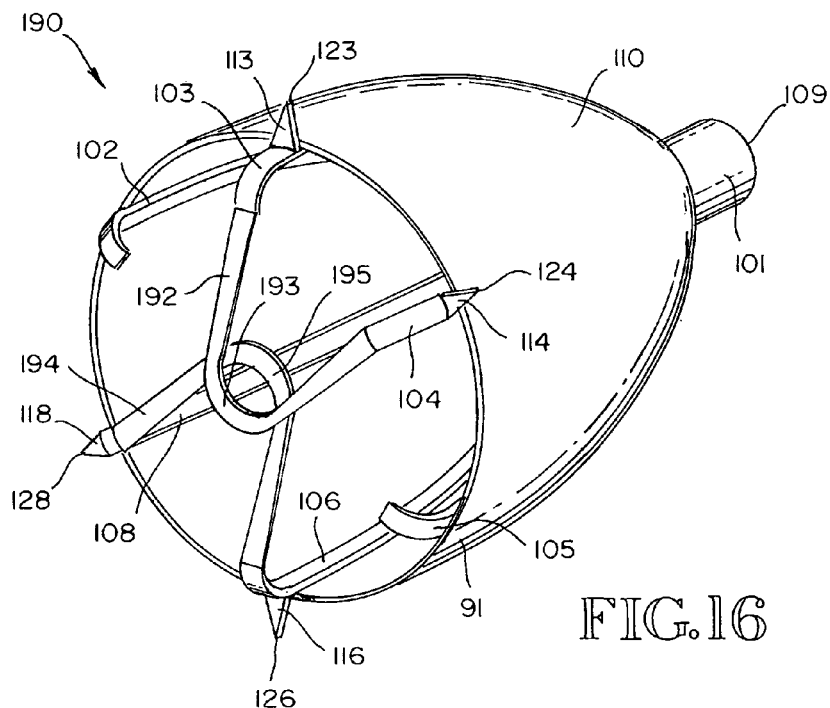
FIG. 16 is a perspective view illustrating an alternative embodiment of a removable intra-bronchial device with proximal anchors carried on a peripheral portion of a plurality of support structure members in accord with the present invention.
Figure 17:
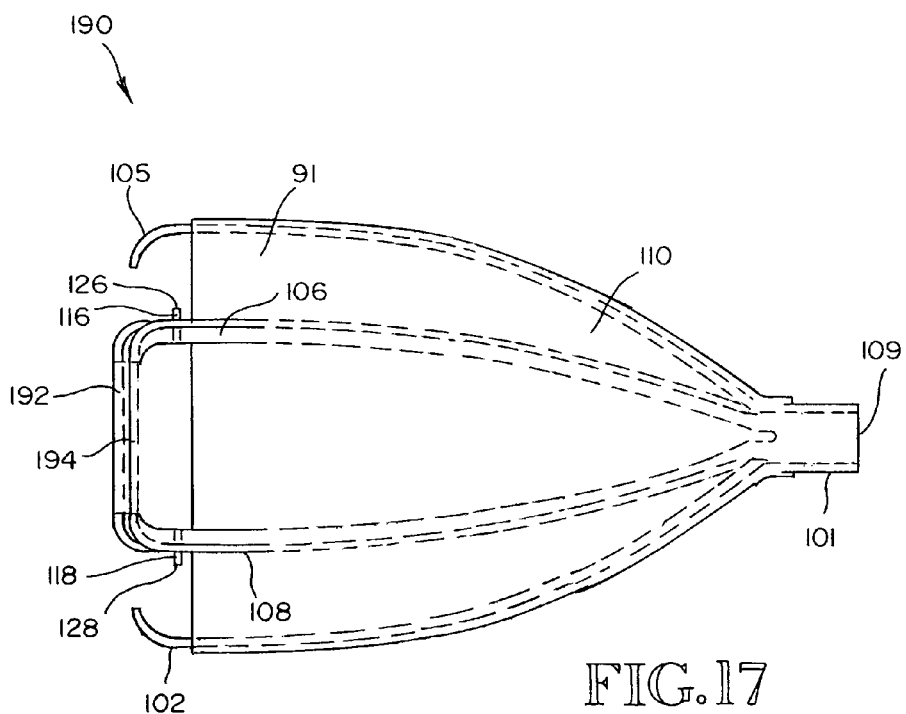
FIG. 17 is a side view of the device of FIG. 16.

FIGS. 16 and 17 illustrate a removable intra-bronchial device with proximal anchors carried on a peripheral portion of a plurality of support structure members in accord with the present invention. FIG. 16 is a perspective view, as the device would appear when fully deployed in an air passageway. FIG. 17 is a side view of FIG. 16. In a preferred embodiment, the support structure 101 of intra-bronchial device 190 includes six support members, with two opposing pairs of support members carrying anchors and each member of a pair being joined together by a retracting member. Intra-bronchial device 190 includes a support structure 101 having a central support structure 109 and support members 102, 103, 104, 105, 106, and 108; four anchors 113, 114, 116, and 118 having anchor ends 123, 124, 126, and 128 respectively; two "U" shaped retracting members 192 and 194 having an apex 193 and 195 respectively; and obstructing member 110. As shown in FIG. 17, the support members extend in a curvilinear manner from the attachment at the central support structure 109 such that an umbrella or substantially parabolic shape is defined. In addition, as also shown in FIG. 17, the free ends of the support members 102, 103, 104, 105, 106, 108 are bent radially inwards. In other words, the illustrated support members 102, 104, 105, 106, 108 comprise tips at their free ends that are angled radially inwards.

Intra-bronchial device 190 is generally similar in construction, operation, placement, and removal to the intra-bronchial device 150 of FIG. 9. Support structure 101 is a tubular member, preferably hypodermic needle tubing, or stainless steel, Nitinol, or other suitable material having a memory of its original shape and resiliency to return the material to that shape. Support members 102, 103, 104, 105, 106, and 108, and central support structure 109 may be formed by laser cutting a single piece of hypodermic needle tubing lengthwise, and bending the support members to a required shape. Support members 102, 103, 104, 105, 106, and 108 are generally similar to each other. Anchors 113, 114, 116, and 118 are disposed on support members 103, 104, 106, and 108, respectively, in any manner available in the art. Anchors 113-118 are disposed on support members 103, 104, 106 and 108 to be located proximally of obstructing member 110, and to engage an air passageway wall when intra-bronchial device 190 is deployed.

"U" shaped retracting member 192 is coupled to support members 103 and 104, and "U" shaped retracting member 194 is coupled to support members 106 and 108. "U" shaped retracting members 192 and 194 may be constructed of any material suitable for use within a patient, and may or may not be resilient as required by the particular embodiment. When intra-bronchial device 190 is fully deployed in an air passageway, the "U" shaped retracting members 192 and 194 are arranged opposite each other, and they partially overlap, with the apex of one lying within a space bounded by the "U" shape of the other member. In the deployed configuration, increasing the distance between apex 193 and apex 195 moves support member pairs 103-104 and 106-108 centrally.

In operation, when intra-bronchial device 190 is compressed for insertion into a catheter lumen and placement in an air passageway, support members 102, 103, 104, 105, 106, and 108 are collapsed centrally into a first configuration. This causes the anchor ends 123-124, and 126-128 to move centrally.

When intra-bronchial device 190 is deployed from the catheter lumen, the memory and resiliency of the support member pairs 103,104 and 106,108 impart a force that moves the anchors 113 and 114, and 116 and 118, and their anchor ends 123 and 124, and 126 and 128 into a second configuration, which is the deployed configuration to engage air passageway wall. In addition, deployment of intra-bronchial device 190 may include a step of forcibly decreasing the distance between apexes 193 and 195 to forcibly move the anchors 113 and 114, and 116 and 118 into engagement with the wall of the air passageway. While the anchors 113 and 114, and 116 and 118 of this embodiment do not include stops, the expansive or peripheral movement of the anchors will be limited by obstructing member 90. This may limit the piercing of the air passageway wall by anchors 113 and 114, and 116 and 118.

In an alternative embodiment, support member pairs 103, 104 and 106,108 may be compressed for insertion into a catheter lumen by a device that increases the distance between apex 193 and apex 195. Such a device could be a tool with spreading jaws, or a tapered member inserted between the apexes. The device could be left in engagement after insertion into the catheter, and then withdrawn to allow support member pairs 103-104 and 106-108 to move apart and engage their anchors into the wall of the air passageway.

For removal, a retractor device is deployed from a catheter lumen to engage apex 193 and 195, and restrain intra-bronchial device 190. The retractor device may be any device that fits into the space defined by apexes 193 and 195 when the intra-bronchial device 190 is in its fully deployed configuration. The retractor device is used to increase the distance between apexes 193 and 195 until anchors 113-114 and 116-118, and anchor ends 123-124 and 126-128 are released from the air passageway wall. This collapses the anchors into to the first configuration for removal. Intra-bronchial device 190 is then further collapsed, and drawn into the catheter by pulling on the retractor device. This additionally collapses support structure 101 and obstructing member 110 into the first position so that they may be fully drawn into the catheter. Once drawn into the catheter, intra-bronchial device 190 may be removed from the air passageway and the patient.

Figure 18:
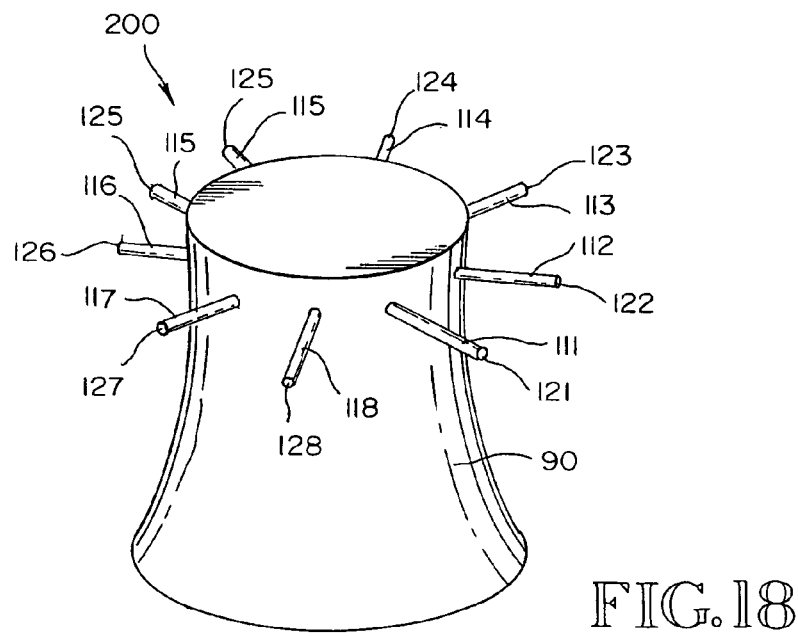
FIG. 18 is a perspective view of a device in its deployed state with anchors carried on an obstructing member, in accordance with an alternative embodiment of the invention.

FIG. 18 is a perspective view of an intra-bronchial device 200 with anchors carried on an obstructing member as the device would appear when fully deployed in an air passageway, in accordance with an alternative embodiment of the invention. Intra-bronchial device 200 includes an obstructing member 90, anchors 111, 112, 113, 114, 115, 116, 117, and 118 (hereafter collectively referred to as anchors 111-118), and anchor ends 121, 122, 123, 124, 125, 126, 127, and 128 (hereafter collectively referred to as anchor ends 121-128).

Obstructing member 90 may be a single piece made from a collapsible, resilient material, such as silicone, polyurethane, rubber, or foam, and typically will be collapsible to at least one-half of its expanded size. In an alternative embodiment, obstructing member 90 may include multiple pieces, some being of collapsible material. In a further alternative embodiment, obstructing member 90 may include a membrane carried by a support structure such as described in conjunction with FIGS. 5-17.

Anchors 111-118 comprise material having memory of an original shape, and resiliency to return the material to that hape, and typically have a diameter small enough that penetration through an air passageway wall may not adversely effect a patient. Anchors 111-118 may be 0.003-inch diameter 316 stainless steel with a wire spring temper, Nitinol, or other resilient material. Anchor ends 121-128 may be shaped to promote or control piercing of the air passageway wall. In an alternative embodiment, the length of the anchors 111-118 may be limited to allow the anchors 111-118 to penetrate into but not through the air passageway wall. In the preferred embodiment illustrated in FIG. 18, the anchors include four pieces of material pushed through obstructing member 90. The four pieces would lie in approximately the same cross-sectional plane, and cross each other at approximately the centerline of obstructing member 90, with approximately equal portions of the anchor material projecting from opposite sides of the obstructing member 90. In this embodiment, for example, anchors 112 and 116 would be opposite portions of a single piece of material. Anchors 111-118 may be secured to control their position. For example, a centerline opening may be made in obstructing member 90 exposing the several pieces of anchoring material. The several pieces of material could them be joined together, or to obstructing member 90, at a location within the centerline opening by an adhesive, crimping, welding, or other method of mechanically joining materials known to those in the art.

In an alternative embodiment, the anchors may be formed by individual pieces of material. The individual pieces of material may be coupled to obstructing member 90 either at its periphery, or within its periphery.

Figure 19:
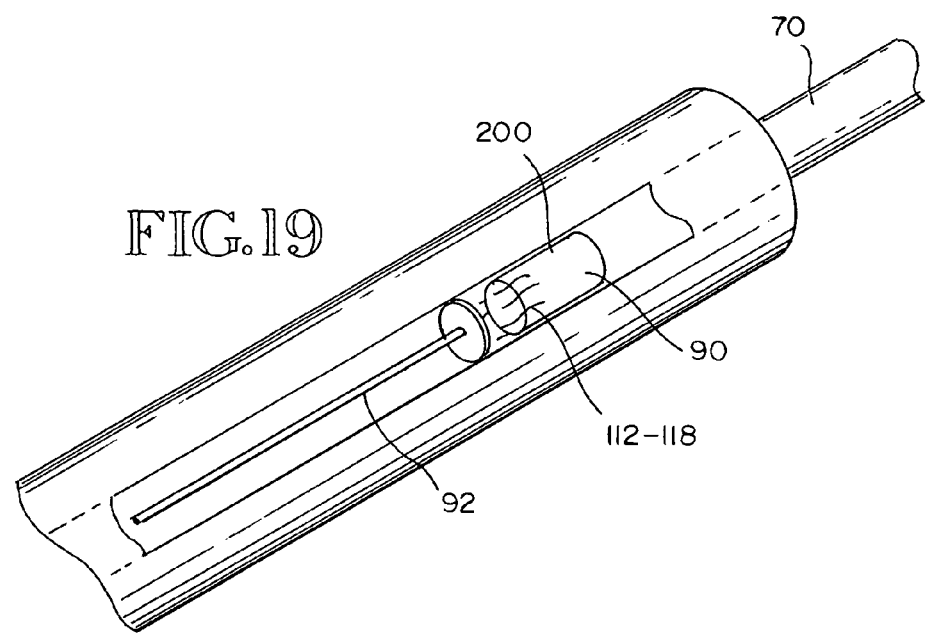
FIG. 19 is a partial longitudinal sectional view of the device of FIG. 18 in a collapsed state and located into a lumen for placement in an air passageway.

FIG. 19 is a partial longitudinal sectional view of the intra-bronchial device of FIG. 18 collapsed and located into a delivery catheter lumen for placement in an air passageway to collapse a lung portion associated with the air passageway, in accordance with the present invention. Intra-bronchial device 200 is generally placed in an air passageway as described in FIGS. 2 and 3.

More specifically, intra-bronchial device 200 is collapsed and placed into delivery catheter lumen 70. Obstructing member 90 is collapsed into approximately a cylindrical shape. Anchors 111-118 are collapsed to a position in proximity to or against the outer periphery of collapsed obstructing member 90. Intra-bronchial device 200 is inserted into catheter lumen 70, the distal end of which is typically already placed in the air passageway 50 as generally illustrated in FIG. 3. Using stylet 92, intra-bronchial device 200 is advanced through the catheter lumen 70 into the air passageway to where it is to be deployed. Once the point of deployment is reached, intra-bronchial device 200 is expelled from catheter lumen 70, and assumes a deployed shape as illustrated in FIG. 18.

Figure 20:
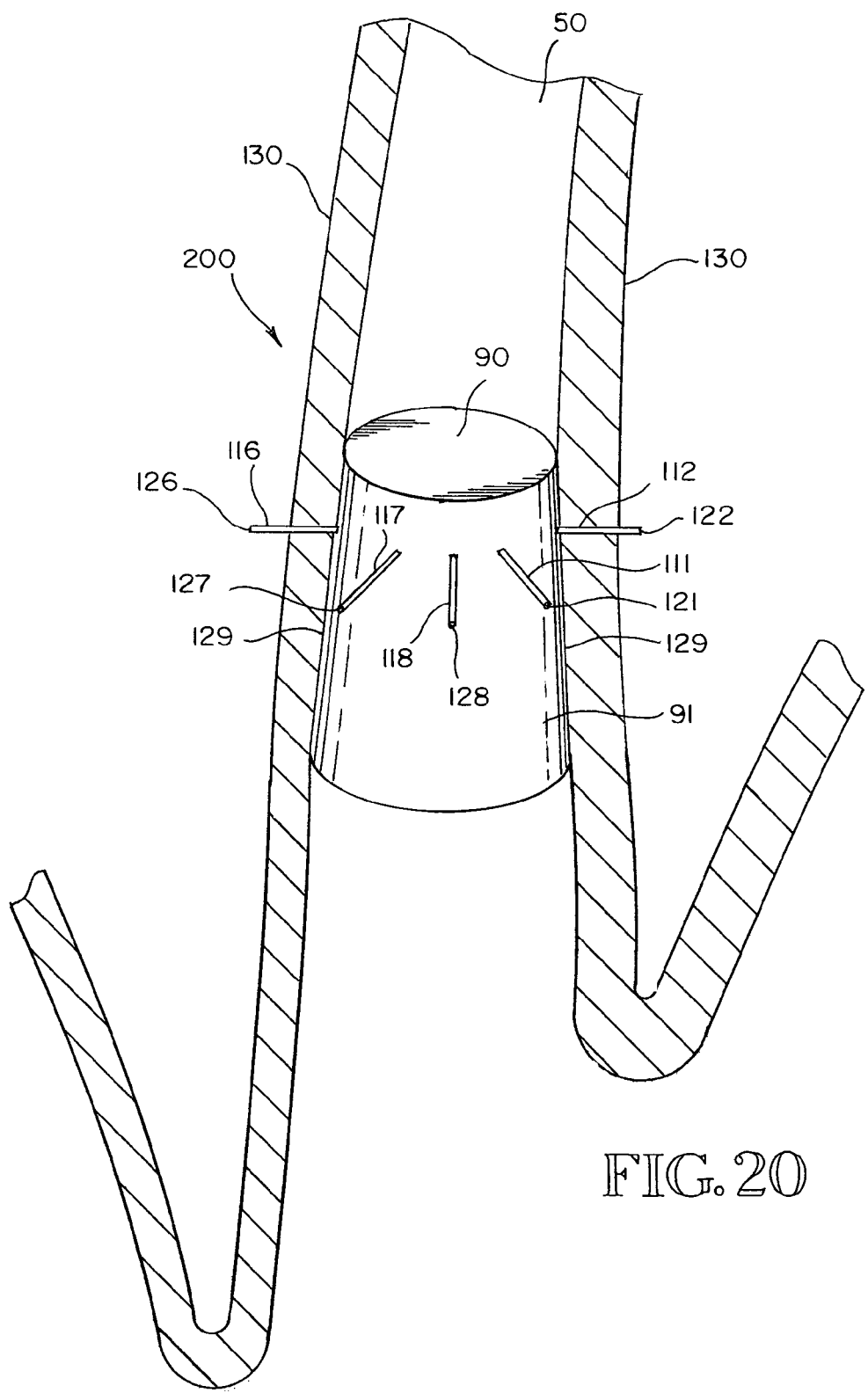
FIG. 20 is a perspective view of the device of FIG. 18 in its deployed and anchored state in an air passageway, in accordance with the present invention.

FIG. 20 is a perspective view of the intra-bronchial device of FIG. 18 in its fully deployed and anchored state in an air passageway, in accordance with the present invention. Intra-bronchial device 200 is illustrated after having been expelled from the catheter lumen in substantially the manner described in conjunction with FIG. 3, and having deployed anchors 112 and 116 by piercing into and through air passageway wall 130 of air passageway 50. The piercing engages the air passageway wall and anchors intra-bronchial device 200 within the air passageway 50.

The resiliency of obstructing member 90 imparts a force to expand the obstructing member 90 from the collapsed state to a deployed state. In its deployed state, obstructing member 90 forms a contact zone 129 with the wall 130 of air passageway 50 preventing air from being inhaled into the lung portion. The resiliency of the anchor members 111-118 moves them from their collapsed state illustrated in FIG. 19 to their deployed state. The resiliency of obstructing member 90 may assist anchor members 111-118 in deployment. In the alternative embodiment where the length of anchors 111-118 is limited to allow the anchors 111-118 to penetrate into but not through the air passageway wall, the anchors penetrate the air passageway wall 150 in the manner illustrated in FIG. 7.

FIGS. 21-24 are side views showing an embodiment of the present invention for removing the intra-bronchial device 200 from air passageway 50. The preclusion of air from being inhaled into the lung portion may be terminated by eliminating the obstructing effect of intra-bronchial device 200. The preclusion of air by the embodiment illustrated in FIG. 18 may be eliminated by releasing anchors 111-118 from the air passageway wall 130.

A bronchoscope 74 is placed in proximity to intrabronchial device 200 in the air passageway 50. A catheter 70 having an internal lumen 71 is fed into the bronchoscope 74 and advanced to the proximal end of the intra-bronchial device 200. A retractor device, such as biopsy forceps 76, capable of gripping a portion of intra-bronchial device 200, is inserted in the catheter 70 of the bronchoscope 74 and advanced to the intra-bronchial device 200. The jaws of the forceps 76 are used to engage a portion of the obstructing member 90. The engagement may collapse a portion of obstructing member 90. The engagement with the obstructing member 90 is maintained and obstructing member 90 is drawn toward the catheter lumen 71 by the forceps 76. The drawing action releases anchors 111-118 from air passageway wall 130. The intra-bronchial device 200 is then drawn into the catheter lumen 71 with the forceps 76. The collapsed device 200 now fully enters the catheter lumen 71 for removal from the patient.

Figure 25:
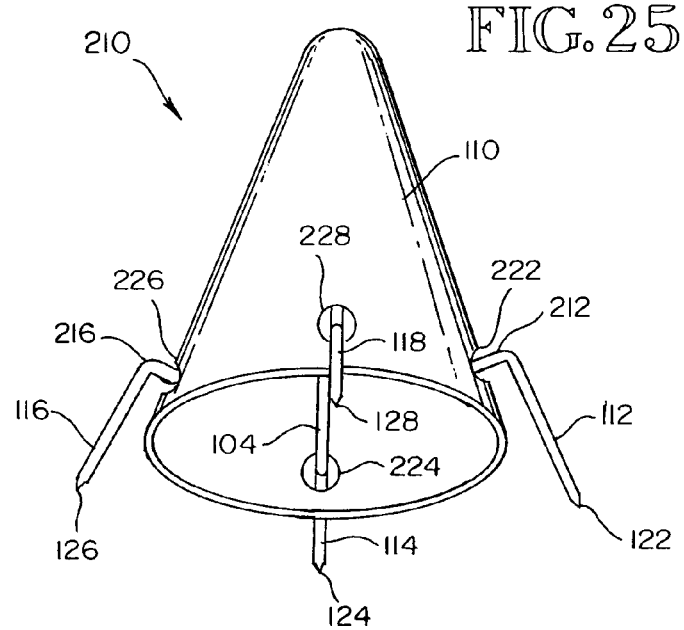
FIG. 25 is a perspective view of a device in its deployed state with anchors carried on the obstructing member, in accordance with an alternative embodiment of the present invention.

FIG. 25 is a perspective view of an intra-bronchial device with anchors projecting from a periphery of an obstructing member as the device would appear when fully deployed, in accordance with an alternative embodiment of the present invention. The intra-bronchial device 210 includes support members 102, 104, 106, and 108; an obstructing member 110; "s" shaped bends 212, 214, 216, and 218; and anchors 112, 114, 116, and 118.

The support members 102, 104, 106, and 108 form a support structure carrying obstructing member 110, and include anchors 112, 114, 116, and 118; and anchor ends 122, 124, 126, and 128, respectively. The support members 102, 104, 106, and 108 may be tubular members, and are preferably hypodermic needle tubing. Support members 102, 104, 106, and 108 form a support structure by being joined together at a location toward the distal portion of intra-bronchial device 210. They may be joined by a mechanical method, such as by crimping, or by other methods such as adhesive or welding. In an alternative embodiment, two support members may be formed from a single piece of material by bending it in the middle. Support members 102, 104, 106, and 108 are generally similar to each other. The support members are preferably formed of stainless steel, Nitinol, or other suitable material having a memory of its original shape, and resiliency to return the material to that shape.

Anchors 112, 114, 116, and 118 are extensions of support members 102, 104, 106, and 108. The anchors are formed by forming "s" shaped bends 212, 214, 216, and 218 in proximal portions of the support members. Anchor ends 122, 124, 126, and 128 may be shaped to promote piercing the air passageway wall.

Figure 26:
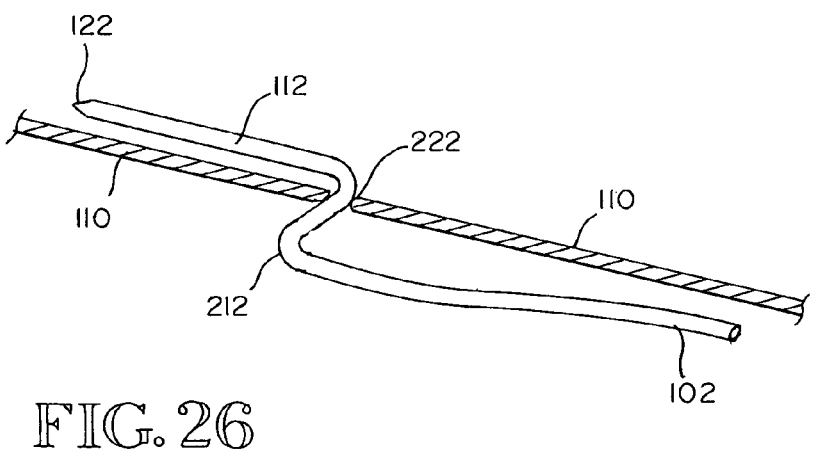
FIG. 26 illustrates the placement and securing of the obstructing member of the device of FIG. 25 to a support member.

The obstructing member 110 is carried on the support structure formed by support members 102, 104, 106, and 108. Obstructing member 110 includes a flexible membrane open in the proximal direction and which may be formed of silicone or polyurethane, for example. The obstructing member 110 includes openings 222, 224, 226, and 228 sized to sealingly admit the "s" shaped bends 212, 214, 216, and 218 of support members 102, 104, 106, and 108, respectively. FIG. 26 illustrates the placement and securing of the obstructing member 110 to support member 102 at "s" bend 212.

Obstructing member 110 is fitted over the anchor end 122 and anchor 112 at opening 222. Obstructing member 110 engages the peripheral apex of the "s" shaped bend 212, and thus secures it. The obstructing member 110 is placed and secured to the other "s" bends 214, 216, and 218 in a similar manner.

Obstructing member 110 may be loosely carried on support members 102, 104, 106, and 108 such that it expands on inhalation to form a seal against a wall of the air passageway, and contracts on exhalation to allow air and mucociliary transport from the collapsed lung. This provides a one-way valve function.

Figure 27:
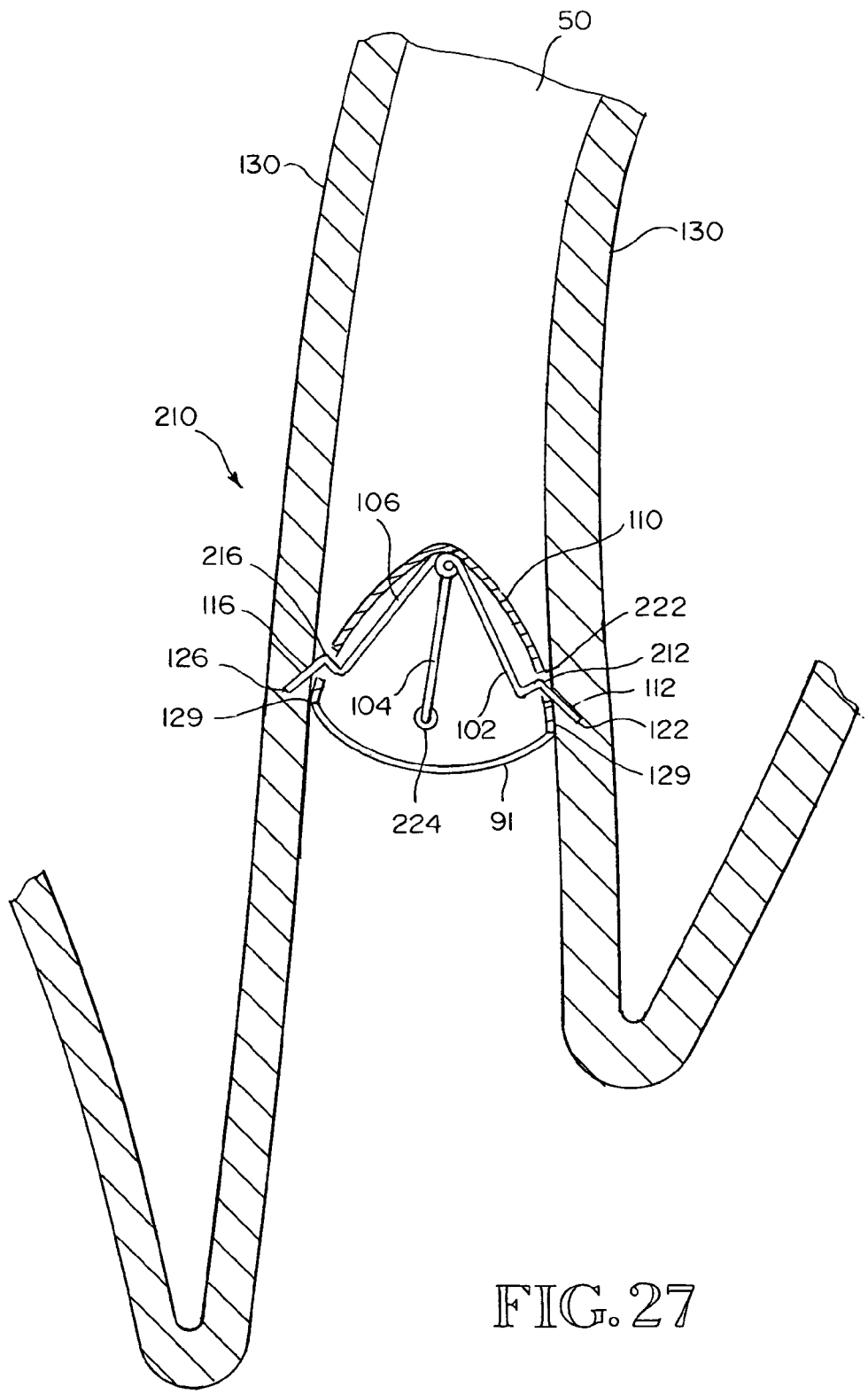
FIG. 27 is a perspective view of the intra-bronchial device of FIG. 25 fully deployed and anchored in an air passageway, in accordance with the present invention.

FIG. 27 is a perspective view of the intra-bronchial device of FIG. 25 fully deployed and anchored in an air passageway, in accordance with the present invention. Intra-bronchial device 210 is illustrated after having been expelled from the catheter lumen in substantially the manner described in conjunction with FIG. 3, and having deployed anchors 112, 114, 116, and 118 by piercing into air passageway wall 130 of air passageway 50. The piercing engages the air passageway wall and anchors intra-bronchial device 210 within the air passageway 50.

Deploying obstructing member 210 is much like opening an umbrella. Upon deployment, the memory and resiliency of the support members 102, 104, 106, and 108, expand obstructing member 210. The expanded obstructing member 210 forms a contact zone 129 with the wall 130 of the air passageway 50 to prevent air from being inhaled into the lung portion to collapse the lung portion. Simultaneously upon deployment, the memory and resiliency of the support members 102, 104, 106, and 108 impart a force on the anchor ends 122, 124, 126, and 128, and urge the anchors 112, 114, 116, and 118 to engage air passageway wall 130 by piercing. The anchors pierce into and become embedded in the wall 130 of the air passageway 50, preferably without projecting through the wall 130. Stops may be incorporated into the anchors to limit piercing of the wall 130. For example, the "s" bends 212, 214, 216, and 218 may form a stop.

The preclusion of air from being inhaled into the lung portion may be terminated by eliminating the obstructing effect of intra-bronchial device 210. The preclusion of air by the embodiment illustrated in FIGS. 25-27 may be eliminated by releasing anchors 112, 114, 116, and 118 from the air passageway wall 130. The anchors are released and the intra-bronchial device 210 is removed from air passageway 50 in substantially the same manner described in conjunction with FIGS. 7, and 21-24. The forceps are used to engage a portion of intra-bronchial device 210, and maneuvered to release anchors 112, 114, 116, and 118 from the air passageway wall 130. Intra-bronchial device 210 is then drawn into the catheter for removal from the patient. Alternatively, the obstructing effect may be eliminated by engaging the obstructing member 210, releasing it from the support members 102, 104, 106, and 108, and drawing obstructing member 110 into the catheter for removal from the patent.

Although the present invention has been described in considerable detail with reference to certain preferred embodiments, other embodiments are possible. Therefore, the spirit or scope of the appended claims should not be limited to the description of the embodiments contained herein. It is intended that the invention resides in the claims hereinafter appended.

What is claimed is:

1. A method of treating a lung, the method comprising:
providing an air passageway device comprising an obstructing member having a distal end and a proximal end, the obstructing member comprises a support assembly having a plurality of support members, the plurality of support members extending in a proximal direction from the distal end, a resilient membrane coupled to the support members and when deployed in an air passageway the resilient membrane is dimensioned to communicate with a portion of the lung to preclude air from being inhaled, said air passageway device further comprising at least one anchor that anchors said obstructing member when said anchor is deployed, the at least one anchor positioned distal to the distal end of the obstructing member, the plurality of support members comprising proximal tips that are curved toward an axial center of the obstructing member, the plurality of support members curved between the distal end and the proximal tips to form a concave side and convex side, wherein the concave side faces the axial center of the obstructing member and the convex side faces a wall of the air passageway;
placing said obstructing member in the air passageway with a delivery catheter;
deploying said anchor; and
disengaging said delivery catheter from said obstructing member, wherein said obstructing member substantially precludes air from being inhaled after said delivery catheter is disengaged from said obstructing member.

2. The method of claim 1, wherein said anchor is releasable for removal of said obstructing member.

3. The method of claim 1, wherein said obstructing member forms a one-way valve when deployed.

4. The method of claim 1, wherein a portion of said obstructing member is collapsible.

5. The method of claim 1 further comprising removing said obstructing member by drawing said obstructing member proximally.

6. The method of claim 1 further comprising drawing said anchor proximally and removing said obstructing member.

7. The method of claim 6, wherein said device comprises a plurality of anchors and said plurality of anchors are drawn proximally.

8. The method of claim 1, wherein said device comprises a plurality of anchors.

* * * * *